US008546356B2

(12) United States Patent
Soula et al.

(10) Patent No.: US 8,546,356 B2
(45) Date of Patent: Oct. 1, 2013

(54) ADMINISTRATION FORM OF OSTEOGENIC PROTEIN COMPLEXES

(75) Inventors: Olivier Soula, Meyzieu (FR); Remi Soula, Lyons (FR); Gerard Soula, Meyzieu (FR)

(73) Assignee: ADOCIA, Lyons (FR)

( * ) Notice: Subject to any disclaimer, the term of this patent is extended or adjusted under 35 U.S.C. 154(b) by 460 days.

(21) Appl. No.: 12/591,442

(22) Filed: Nov. 19, 2009

(65) Prior Publication Data

US 2010/0166867 A1 Jul. 1, 2010

Related U.S. Application Data

(60) Provisional application No. 61/116,144, filed on Nov. 19, 2008, provisional application No. 61/213,939, filed on Jul. 31, 2009.

(30) Foreign Application Priority Data

Jul. 31, 2009 (FR) ...................................... 09 03803

(51) Int. Cl.
*A61K 31/721* (2006.01)
*C08B 37/02* (2006.01)
(52) U.S. Cl.
CPC ........... *A61K 31/721* (2013.01); *C08B 37/0021* (2013.01)
USPC ........................................ 514/59; 536/123.12
(58) Field of Classification Search
None
See application file for complete search history.

(56) References Cited

U.S. PATENT DOCUMENTS

| | | | |
|---|---|---|---|
| 2,387,201 A | 10/1945 | Weiner | |
| 4,455,256 A | 6/1984 | Urist | |
| 4,826,818 A | 5/1989 | Mori et al. | |
| 5,650,176 A | 7/1997 | Lee et al. | |
| 5,683,461 A | 11/1997 | Lee et al. | |
| 6,946,443 B2 * | 9/2005 | Blanchat et al. | 424/423 |
| 2004/0220143 A1 | 11/2004 | Byun et al. | |
| 2005/0112091 A1 * | 5/2005 | DiMauro et al. | 424/85.1 |
| 2007/0015701 A1 | 1/2007 | Zalipsky et al. | |
| 2008/0014250 A1 | 1/2008 | Soula et al. | |
| 2008/0234227 A1 | 9/2008 | Soula et al. | |
| 2009/0048412 A1 | 2/2009 | Soula et al. | |
| 2009/0155320 A1 | 6/2009 | Rudin et al. | |
| 2009/0291114 A1 | 11/2009 | Soula et al. | |
| 2010/0009911 A1 * | 1/2010 | Soula | 514/12 |
| 2010/0137456 A1 | 6/2010 | Soula et al. | |
| 2010/0167991 A1 | 7/2010 | Soula et al. | |
| 2011/0159068 A1 * | 6/2011 | Soula et al. | 424/422 |

FOREIGN PATENT DOCUMENTS

| | | |
|---|---|---|
| EP | 1 891 984 A1 | 2/2008 |
| FR | 2 861 396 | 4/2005 |
| FR | 2 919 188 | 7/2007 |
| FR | 2 933 306 | 7/2008 |
| FR | 2 914 305 | 10/2008 |
| FR | 2 934 999 A1 | 2/2010 |
| FR | 2 936 800 A1 | 4/2010 |
| WO | WO03/024316 * | 3/2003 |
| WO | WO2007/009477 * | 1/2007 |
| WO | WO 2007/116143 A1 | 10/2007 |
| WO | WO 2009/016131 A1 | 2/2009 |
| WO | WO 2009/127940 A1 | 10/2009 |
| WO | WO 2009/144578 A2 | 12/2009 |
| WO | WO 2010/041119 A1 | 4/2010 |
| WO | WO 2010/058106 A1 | 5/2010 |

OTHER PUBLICATIONS

Krane et al., Identifying genes that regulate bone remodeling as potential therapeutic targets Journal of Experimental Medicine (2001) vol. 201 No. 6 pp. 841-843.*
Gupta et al., "Angiogenesis: a curse of cure?" Postgraduate Medical Journal (2005) vol. 81 pp. 236-242.*
English translation of U.S. Appl. No. 61/193,216, filed Nov. 6, 2008, pp. 1-38.*
Hyunh et al., "Anticoagulant properties of dextranmethylcarboxylate benzylamide sulfate (DMCBSu); a new generation of bioactive functionalized dextran" Carbohydrate Research (2001) vol. 332 pp. 75-83.*
Chen et al., "Novel glycidyl methacrylated dextran (Dex-GMA)/gelatin hydrogel scaffolds containing microspheres loaded with bone morphogenetic proteins: Formulation and characteristics" Journal of Controlled Release (2007) vol. 118, pp. 65-77.*
French Search Report mailed Apr. 27, 2010 issued in French Patent Application No. FR 0903803 (with translation).
International Search Report mailed May 4, 2010 issued in International Patent Application No. PCT/FR2009/001332 (with translation).
Urist, "Bone: Formation by Autoinduction," Science (1965), vol. 150, pp. 893-899.
Scheufler et al., "Crystal Structure of Human Bone Morphogenetic Protein-2 at 2.7 A Resolution," J. Mol. Biol. (1999), vol. 287 pp. 103-115.
Schlunegger et al., "Refined Crystal Structure of Human Transforming Growth Factor β2 at 1 95 A Resolution," J. Mol. Biol. (1993), vol. 231, pp. 445-458.
Israel et al., "Heterodimeric Bone Morphogenetic Proteins Show Enhanced Activity in Vitro and in Vivo," Growth Factors (1996), vol. 13, pp. 291-300.
Mundy et al., "Bone Morphogenetic Proteins," Growth Factors, Dec. 2004, vol. 22, pp. 233-241.

(Continued)

*Primary Examiner* — Eric S Olson
(74) *Attorney, Agent, or Firm* — Oliff & Berridge, PLC

(57) ABSTRACT

Osteogenic compositions composed of a coprecipitate that contains at least one insoluble calcium salt and at least one complex between an osteogenic protein and a polysaccharide, the coprecipitate being in divided form, are described. Kits are also described, as are a process for preparing the coprecipitate in divided form, containing at least one insoluble calcium salt and at least one complex between an osteogenic protein and a polysaccharide.

46 Claims, No Drawings

(56) References Cited

OTHER PUBLICATIONS

Cheng et al., "Osteogenic Activity of the Fourteen Types of Human Bone Morphogenetic Proteins (BMPs)," Bone and Joint Surgery (2003), pp. 1544-1552.
Seeherman et al., "Bone Morphogenetic Protein Delivery Systems," Spine, vol. 27, No. 16S, pp. S16-S23.
Bohner, "Calcium Orthophosphates in Medicine: From Ceramics to Calcium Phosphate Cements," Injury (2000), vol. 31, S-D37-S-D47.
Boden et al., "Use of Recombinant Human Bone Morphogenetic Protein-2 to Achieve Posterolateral Lumbar Spine Fusion in Humans," Spine, vol. 27, No. 23, pp. 2662-2673 (2002).
Kim et al., "Characterization of a Calcium Phosphate-Based Matrix for rhBMP-2," Methods in Molecular Biology (2004), vol. 238, pp. 49-64.
Hoffman, "Hydrogels for Biomedical Applications," Adv. Drug Deliv. Rev. (2002), vol. 43, pp. 3-12.
Peppas et al., "Hydrogels in Pharmaceutical Formulations," Eur. J. Pharm. Biopharm. (2000), vol. 50, pp. 27-46.
Alhaique et al., "Polysaccharide Hydrogels for Modified Release Formulations," J. Control. Release (2007), vol. 119, pp. 5-24.
Lawrence et al., "rhBMP-2 (ACS and CRM Formulations) Overcomes Pseudarthrosis in a New Zealand White Rabbit Posterolateral Fusion Model," Spine, vol. 32, No. 11, pp. 1206-1213 (2007).
Yao et al., "Evaluation of Insoluble Bone Gelatin as a Carrier for Enhancement of Osteogenetic Protein-1-Induced Intertransverse Process Lumbar Fusion in a Rabbit Model," Spine, vol. 33, No. 18, pp. 1935-1942 (2008).
Magit et al., "Healos/Recombinant Human Growth and Differentiation Factor-5 Induces Posterolateral Lumbar Fusion in a New Zealand White Rabbit Model," Spine, vol. 31, No. 19, pp. 2180-2188 (2006).
U.S. Appl. No. 61/129,023 in the name of Olivier Soula filed May 30, 2008.
U.S. Appl. No. 61/129,617 in the name of Olivier Soula filed Jul. 8, 2008.
U.S. Appl. No. 61/129,011 in the name of Gerard Soula filed May 30, 2008.
U.S. Appl. No. 61/129,618 in the name of Gerard Soula filed Jul. 8, 2008.
U.S. Appl. No. 61/129,616 in the name of Olivier Soula filed Jul. 8, 2008.
U.S. Appl. No. 61/129,012 in the name of Olivier Soula filed May 30, 2008.
U.S. Appl. No. 61/193,217 in the name of Olivier Soula filed Nov. 6, 2008.
U.S. Appl. No. 61/193,216 in the name of Olivier Soula filed Nov. 6, 2008.
Dohzono et al., "Successful Spinal Fusion by E. coli-Derived BMP-2-adsorbed Porous β-TCP Granules," Clin. Orthop., Relat. Res., 2009, pp. 1-6.
Seeherman et al., "A Review of Preclinical Program Development for Evaluating for Evaluation Injectable Carriers for Osteogenic Factors," J. of Bone and Joint Surgery, 2003, vol. 85-A, Supp. 3, pp. 96-108.
Wang et al., "Controlled-Release of rhBMP-2 Carriers in the Regeneration of Osteonecrotic Bone," Biomaterials, 2009, vol. 30 pp. 4178-4186.
Dawson et al., "Recombinant Human Bone Morphogenetic Protein-2 on an Absorbable Collagen Sponge with an Osteoconductive Bulking Agent in Posterolateral Arthrodesis with Instrumentation," J. of Bone and Joint Surgery, 2009, pp. 1604-1613.
U.S. Appl. No. 12/461,326, filed Aug. 7, 2009 in the name of Remi Soula.
Chubinskaya, et al., "OP-1/BMP-7 in cartilage report," International Orthopaedics (SICOT), 2007, vol. 31, pp. 773-781.
Zeisberg, et al., "Bone Morphogenic Protein-7 Induces Mesenchymal to Epithelial Transition in Adult Renal Fibroblasts and Facilitates Regeneration of Injured Kidney," The Journal of Biological Chemistry, vol. 280, No. 9, Issue of Mar. 4, 2005, pp. 8094-8100.

Sugimoto, et al., "BMP-7 Functions as a novel hormone to facilitate liver regeneration," The FASEB Journal, Research Communication, Jan. 2007, vol. 21, pp. 256-264.
Kinoshita, et al., "Adenovirus-mediacted expression of BMP-7 suppresses the development of liver fibrosis in rats," Gut, 2007, vol. 56, pp. 706-714.
Gressner, et al., "Changing the pathogenetic roadmap of liver fibrosis? Where did it start; where will it go?," Journal of Gastroenterology and Hepatology, 2008, vol. 23, pp. 1024-1035.
Saika, et al., "Therapeutic effects of adenoviral gene transfer of bone morphogenic protein-7 on a corneal alkali injury model in mice," Laboratory Investigation (2005), vol. 85, pp. 474-486.
Chang, et al., "Intravenous Administration of Bone Morphogenetic Protein-7 After Ischemia Improves Motor Function in Stroke Rats," Stroke (2003), vol. 34, pp. 558-564.
Zeisberg, et al., "Endothelial-to-mesenchymal transition contributes of cardiac fibrosis," Nature Medicine, 2007, vol. 13, No. 8, pp. 952-961.
Myllarniemi, et al., "Gremlin-mediated Decrease in Bone Morphogenetic Protein Signaling Promotes Pulmonary Fibrosis," American Journal of Respiratory and Critical Care Medicine, 2008, vol. 177, pp. 321-329.
Derivero Vaccari, et al., "Neuroprotective effects of bone morphogenetic protein 7 (BMP7) treatment after spinal cord injury," Neuroscience Letters 465, 2009, pp. 226-229.
Harvey, et al., "Neurotrophic effects of bone morphogenetic protein-7 in a rat model of Parkinson's desease," Brain Research 1022, 2004, pp. 88-95.
Moreno-Miralles, et al., "New Insights into bon morphogenetic protein signaling: focus on angiogenesis," Current Opinion in Hematology, 2008, vol. 16, pp. 195-201.
David, et al., "Emerging role of bone morphogenetic proteins in angiogenesis," Cytokine & Growth Factor Review, 2009, vol. 20, pp. 203-212.
Hwang, et al., "Immunogenicity of osteogenic protein 1: results from a prospective, randomized, controlled, multicenter pivotal study of uninstrumented lumbar posterolateral fusion," J Neurosurg Spin, 2010, vol. 13, pp. 484-493.
Vukicevic, et al., "Systemic administration of bone morphogenetic proteins," Birkhauser Verlag Basel, 2008, pp. 317-337.
Swencki-Underwood, et al., "Expression and characterization of a human BMP-7 variant with improved biochemical properties," Protein Expression & Purification, 2008, vol. 57, pp. 312-319.
Sanchez-Chaves, et al., "Poly (vinyl alcohol) functionalized by monosuccinate groups. Coupling of bioactive amino compounds," Polymer, 1998, vol. 39, No. 13, pp. 2751-2757.
Pal, et al., "Molecular mechanism of physical gelation of hydrocarbons by fatty acid amides of natural amino acids," Tetrahedron, 2007, vol. 63, pp. 7334-7348.
Paul, et al., "N,N[1]-Carbonyldiimidazole in Peptide Synthesis. 111.[1] A synthesis of Isoleucine-5 Angiotensin II Amide-1," Organic Chemical, 1962, vol. 27, pp. 2094-2099.
Dale, et al., "The Process Development of a Scaleable Route to the PDE5 Inhibitor UK-357,903," Organic Process Research & Development, 2002, vol. 6, pp. 767-772.
Mire-Sluis, et al., "Recommendations for the design and optimization of immunoassays used in the detection of host antibodies against biotechnology products," Journal of Immunological Methods, 2004, vol. 289, pp. 1-16.
Hwang, et al., "Immunogenicity of Bone Morphogentic Proteins," J. Neurosurg Spine, 2009, vol. 10, pp. 443-451.
Knolker, et al., "Isocyanates, Part 4,[10] Convenient Phosgene-Free Method for the Synthesis and Derivatization of Enantiopure α-Isocyanato Carboxylic Acid Esters," Synlett, Aug. 1997, pp. 925-928.
French Search Report dated Oct. 1, 2010 issued in French Patent Application No. 737360.
U.S. Appl. No. 12/950,616 in the name of Reim Soula et al, filed Nov. 19, 2010.
U.S. Appl. No. 13/024,100 in the name of Richard Charvet, et al. filed Feb. 9, 2011.

Written Opinion of the International Searching Authority issued in Application No. PCT/FR2009/001332 dated Jun. 16, 2011.
Office Action dated Dec. 10, 2012 issued in U.S. Appl. No. 12/950,616.

Office Action dated Jun. 26, 2013 issued in U.S. Appl. No. 12/950,616.

* cited by examiner

ADMINISTRATION FORM OF OSTEOGENIC PROTEIN COMPLEXES

The present application is a non-provisional application that claims the benefit of U.S. Provisional Application No. 61/116,144 filed Nov. 19, 2008 and U.S. Provisional Application No. 61/213,939, filed Jul. 31, 2009. The application also claims the priority benefit of French application Ser. No. 09/03803 filed on Jul. 31, 2009.

The present invention relates to the field of osteogenic formulations and more particularly formulations of osteogenic proteins belonging to the family of Bone Morphogenetic Proteins, BMPs.

Bone Morphogenetic Proteins (BMPs) are growth factors involved in osteo-induction mechanisms. BMPs, also known as osteogenic proteins (OPs), were initially characterized by Urist in 1965 (Urist MR. Science 1965; 150, 893). These proteins isolated from cortical bone have the capacity of inducing bone formation in a large number of animals (Urist MR. Science 1965; 150, 893).

BMPs are expressed in the form of propeptides, which, after post-translational maturation, have a length of between 104 and 139 residues. There is large sequence homology between them and they have similar three-dimensional structures. In particular, they contain six cysteine residues involved in intramolecular disulfide bridges forming a "cysteine knot" (Scheufler C. 2004 J. Mol. Biol. 1999; 287, 103; Schlunegger M P, J. Mol. Biol. 1993; 231, 445). Some of them contain a seventh cysteine also involved in an intermolecular disulfide bridge, which is the origin of the formation of the dimer (Scheufler C. 2004 J. Mol. Biol. 1999; 287:103).

In their active form, BMPs assemble into homodimers, or even into heterodimers, as has been described by Israel et al. (Israel D I, Growth Factors. 1996; 13(3-4), 291). Dimeric BMPs interact with transmembrane receptors of BMPR type (Mundy et al. Growth Factors, 2004, 22 (4), 233). This recognition is the origin of an intracellular signal cascade especially involving the Smad proteins, thus resulting in activation or repression of the target genes.

With the exception of BMP 1 and 3, BMPs play a direct and indirect role in the differentiation of mesenchymal cells, causing their differentiation into osteoblasts (Cheng H., J. Bone and Joint Surgery, 2003, 85A 1544-1552). They also have chemotactic properties and induce proliferation, differentiation and angiogenesis.

Certain recombinant human BMPs, and especially rhBMP-2 and rhBMP-7, have clearly shown a capacity to induce bone formation in vivo in man and have been approved for certain medical applications. Thus, recombinant human BMP-2, dibotermine alpha according to the international nonproprietory name, is formulated in products marketed under the name InFUSE® in the United States and InductOs® in Europe. This product is prescribed in the fusion of lumbar vertebrae and tibial bone regeneration for "non-union" fractures. In the case of InFUSE® for the fusion of lumbar vertebrae, the surgical intervention consists firstly in soaking a collagen sponge with a solution of rhBMP-2, and then placing the sponge in a hollow cage, LT cage, implanted beforehand between the vertebrae.

Recombinant human BMP-7, eptotermine alpha according to the international nonproprietory name, has the same therapeutic indications as BMP-2 and is the basis of two products: OP-1 Implant for open fractures of the tibia, and OP-1 Putty for the fusion of lumbar vertebrae. OP-1 Implant is composed of a powder containing rhBMP-7 and collagen to be taken up in a 0.9% saline solution. The paste obtained is then applied to the fracture during a surgical intervention. OP-1 Putty is in the form of two powders: one containing rhBMP-7 and collagen, the other carboxymethylcellulose (CMC). During a surgical intervention, the CMC is reconstituted with a 0.9% saline solution and mixed with the rhBMP-7 and the collagen. The paste thus obtained is applied to the site to be treated.

The administration of osteogenic proteins is a major problem on account of their instability and of the need that arises to obtain osteogenic formulations containing a minimal amount of osteogenic protein. This is to avoid the side effects generated by high concentrations of these proteins, and also on account of the cost of these proteins.

Many formulations have been and are being developed, for instance those cited in the review by Seeherman (Seeherman, H. et al., Spine 2002, 27 (16 Suppl. 1), S16-S23), in which the importance of the nature of the delivery system is emphasized.

The delivery systems used must make it possible to increase the retention time of the proteins at the site of administration, to obtain total release of the amount of protein used and to avoid an overly abrupt release that may lead to diffusion outside the site of administration.

The delivery system used must also be able to serve as a matrix for bone growth at the site to be treated, while at the same time defining the limits of this bone growth at the site to be treated.

Four types of material are used in delivery systems at the present time: natural polymers, synthetic polymers, inorganic materials, and mixtures of these materials.

However, none of the systems developed has made it possible to significantly reduce the dose of BMP. This is associated, inter alia, either with the instability of the protein in the formulation, or with its poor bioavailability on account of the structure of the support.

As regards natural polymers, collagen, hyaluronans, fibrin, chitosans, alginates and other natural polysaccharides are used.

Although recombinant collagen-based sponges make it possible to overcome most of the known drawbacks of this natural polymer, the introduction of osteogenic protein into the sponges is not satisfactory at the present time.

The other natural polysaccharides in the form of hydrogels essentially have the defect of being resorbed too quickly, unless they are crosslinked beforehand in the form of gels, which leads to the same drawbacks as those mentioned previously for the collagen sponges.

As regards synthetic polymers, the ones most commonly used are poly($\alpha$-hydroxy acid) polymers such as polylactide (PLA), polyglycolide (PLG) and copolymers thereof (PLGA).

The major drawbacks of these polymers are the lowering of the pH due to their degradation and the inflammation reactions they may induce.

As regards inorganic materials, delivery systems combining calcium phosphates with a osteo-inducing protein have been developed.

Among these, mention will be made of calcium phosphate-based ceramics, such as hydroxyapatite (HAP) and tricalcium phosphate (TCP), and "non-ceramic" calcium phosphates, for instance calcium phosphate-based cements (CPCs).

It has been known since the 1970s that calcium phosphate ceramics may be of value in bone reconstruction, as is recalled in the review by M. Bohner (Bohner, M., Injury 2000, 31 Suppl. 4, 37-47).

However, it is accepted that the effective dose of BMP-2 is higher in a ceramic than in a collagen sponge. A clinical study of posterolateral fusion in man (Boden, S. D. et al., Spine 2002, 27 (23), 2662-2673) reports that the dose of BMP-2 (40 mg) is higher with BCP granules (60% HAP and 40% TCP), a product developed by the company Medtronic Sofamor, than in a collagen sponge not containing calcium phosphate (12 mg).

In order to overcome this drawback, a very large number of systems have been developed based on non-ceramic calcium phosphate, among which are calcium phosphate cements. Cements were discovered in the 1980s by Brown and Chow and correspond to the following definition: "Calcium phosphate cements are consisted of an aqueous solution and of one or more calcium phosphates. When mixed together, the calcium phosphate(s) dissolve(s) and precipitate(s) as a less soluble calcium phosphate salt. During the precipitation, the calcium phosphate crystals enlarge and overlap, which leads to the mechanical rigidity of the cement." (Bohner, M., Injury 2000, 31 Suppl. 4, 37-47).

An article by Kim (Kim, H. D. et al., Methods Mol. Biol. 2004, 238, 49-64) describes the use of a cement developed by the company Etex, alpha-BSM, with BMP-2. This novel product does indeed lead to osteo-inducing activity of the matrix.

However, the BMP-2 introduced into this matrix loses a large part of its activity, leading to the need to increase the amount of BMP-2 incorporated. Thus, a dose of 40 μg of BMP-2 is employed in the model of formation of ectopic bone in rats, instead of the 20 μg of BMP-2 employed in a collagen sponge.

In point of fact, cements have two drawbacks. Firstly, the calcium phosphate(s) that are their precursors must be synthesized beforehand under conditions that are incompatible with proteins. Thus, U.S. Pat. No. 5,650,176 describes the reaction conditions necessary for the preparation of amorphous calcium phosphate, which is one of the compounds of alpha-BSM. These conditions are incompatible with proteins since a very large amount of sodium hydroxide is used. Furthermore, these products require vigorous purification since toxic compounds such as calcium nitrate are used.

Other examples of cements such as those described by the company Graftys in patent EP 1 891 984 A1 are obtained under conditions that are incompatible with proteins since dichloromethane is used in the synthesis of the calcium phosphate. The cements described by the company Lisopharm in patent US 2009/0 155 320 are obtained in the presence of calcium hydroxide, which is also incompatible with proteins.

Furthermore, in general, the formation of cement is obtained by reacting a soluble calcium phosphate salt with a solid calcium phosphate salt treated at more than 400° C. in order to make it reactive. The reaction between these two compounds is uncontrolled, mainly exothermic, and leads to a cement of monolithic structure that sequesters protein into its bulk.

In U.S. Pat. No. 563,461, mention is made of the presence of "reactive holes" in the solid, without stating whether this is harmful to the chemical stability of BMP-2.

In order to reduce the losses of protein in the mass of solid formed, it has been described in U.S. Pat. No. 5,650,176 that it is advantageous to add to the reaction mixture effervescent compounds capable of reducing the "monolithic" nature of the cement.

Despite these improvements, the observation cannot be avoided that the amounts of protein required to obtain a bone formation in the model of ectopic rat remain high.

As regards mixed systems, they have not to date made it possible to overcome the problems mentioned above.

In summary, the systems described in the prior art concerning the use of synthetic polymers, natural polymers or inorganic materials such as calcium phosphate cements or ceramics do not fully satisfy the specifications imposed for applications in bone repair.

The Applicant has, to its credit, developed a novel approach that consists in placing osteogenic protein in contact with soluble calcium salts and soluble phosphate salts, which can satisfy the specifications imposed for applications in bone repair.

This novel approach makes it possible, on the one hand, to precipitate the protein, while avoiding any chemical degradation on contact with the reagents present, and, on the other hand, to coprecipitate it with an insoluble calcium salt, preferably calcium phosphate, said coprecipitate being in divided form, which very markedly limits the losses in the mass of solid as observed with cements.

Thus, the Applicant has developed novel osteogenic compositions-composed of a coprecipitate that contains at least one insoluble calcium salt and at least one complex between an osteogenic protein and a polysaccharide, said coprecipitate being in divided form.

The conjunction of these two events makes it possible to obtain very osteogenic formulations containing much smaller amounts of protein.

These novel compositions thus have the advantage of containing smaller amounts of protein, which is the major objective, in order to reduce the side effects after administration to patients.

Furthermore, they allow a reduction in the costs of treatments by reducing the amount of protein, since these proteins are very expensive.

Provisional patent applications 61/129,023 and 61/129,617 in the name of the Applicant are known, the entire contents of which applications are incorporated into the present patent application by reference, which describe and claim osteogenic compositions comprising at least one osteogenic protein, a soluble salt of a divalent cation and a matrix.

Provisional patent applications 61/129,011 and 61/129,618 in the name of the Applicant are known, the entire contents of which applications are incorporated into the present patent application by reference, which describe and claim osteogenic compositions comprising at least one osteogenic protein, at least one angiogenic protein, a soluble salt of a divalent cation, optionally an anionic polysaccharide and optionally a matrix.

The Applicant has disclosed the provisional application Nos. 61/129,616 and 61/129,012, the entire content of which is incorporated into the present patent application by reference, and which describe and claim osteogenic compositions comprising at least one osteogenic protein/anionic polysaccharide complex, a soluble salt of an at least divalent cation and a matrix.

The Applicant has disclosed the provisional application number U.S. 61/193,216, the entire content of which is incorporated into the present patent application by reference, and which describes and claims osteogenic compositions comprising at least one osteogenic protein/anionic polysaccharide complex, a soluble salt of an at least divalent cation and a polymer forming a hydrogel.

Provisional patent application U.S. 61/193,217 filed on Nov. 6, 2008 in the name of the Applicant is known, the entire content of which is incorporated into the present patent application by reference, which describes and claims osteogenic compositions comprising at least one osteogenic protein, a soluble salt of an at least divalent cation, and a polymer forming a hydrogel.

As regards the present invention, the Applicant has also developed the process for preparing the coprecipitate, in divided form, containing at least one insoluble calcium salt and at least one complex between an osteogenic protein and a polysaccharide.

The invention also relates to the formulations, the pharmaceutical products and the medical devices comprising said coprecipitate.

The compositions and kits for using this process and for obtaining the coprecipitate are also inventions described hereinbelow.

The coprecipitation is obtained by:
  precipitation of the complex between the anionic polymer and the osteogenic protein by addition of the solution of a salt of calcium ions,
  precipitation of the calcium ions by addition of a composition comprising at least one soluble salt of an anion capable of forming an insoluble calcium salt at a given pH.

In one embodiment, the coprecipitate results from simultaneous precipitations.

In one embodiment, the coprecipitate results from sequential precipitations.

The complex between the anionic polymer and the osteogenic protein is obtained by adding the anionic polysaccharide solution to the osteogenic protein solution.

In one embodiment, the precipitation of the calcium salt takes place in the form of calcium phosphate, by addition of a soluble phosphate solution.

The nature and form of the coprecipitate may vary as a function of the pH of the solutions placed in contact, since calcium phosphate salts have different solid phases as a function of the pH and as a function of the anionic polysaccharide and the protein constituting the complex.

The invention relates to a coprecipitate consisting of at least one complex between an osteogenic protein and a polysaccharide in its undissolved form and at least one insoluble calcium salt, said coprecipitate being in divided form.

In one embodiment, it also comprises at least one growth factor with chemo-attracting and angiogenic power.

In one embodiment, the insoluble calcium salt is chosen from the group consisting of calcium orthophosphates in anhydrous or hydrated form, alone or as a mixture.

In one embodiment, the coprecipitate also comprises at least one insoluble calcium salt chosen from the group consisting of calcium oxalate, calcium ascorbate, calcium carbonate and calcium sulfate.

Said insoluble calcium salts may be mixed salts formed between cationic calcium ions and anionic ions such as mono-, di- or tribasic phosphates, polysaccharide carboxylates, carbonates, hydroxides and the possible anions borne by bases.

Calcium orthophosphates are salts that result from the neutralization of the various acidities of phosphoric acid with calcium salts, and, according to the literature, the pKa values range from 2.12 to 12.67 at 25° C.

The main insoluble calcium orthophosphates are dicalcium phosphates, DCP, anhydrous or dihydrated, octacalcium phosphates, OCP, tricalcium phosphates, TCP, phosphocalcic hydroxyapatites, HAP or PCA, and tetracalcium phosphate, TTCP.

The anionic polymer/osteogenic protein complexes consist of the complexes described in the application PCT/EP2008/059832 in the name of the Applicant.

They are insolubilized by addition of a soluble calcium salt such as described in the applications FR 08 54621 and 61/129,616.

This coprecipitation as a function of the desired effect is optionally obtained in the presence of a base that allows the pH to be adjusted to a predetermined value.

It makes it possible to obtain a solid chemical composition, in divided form, which especially makes it possible to control the delivery of the osteogenic protein contained in the composition.

This solid chemical composition, in divided form, is obtained spontaneously under room temperature conditions, and its divided state is stable under physiological in vitro conditions.

In one embodiment, the invention consists of a kit for preparing an osteogenic implant comprising at least:
  a—a composition comprising at least one osteogenic protein,
  b—a composition comprising at least one polysaccharide,
  c—a composition comprising at least one soluble calcium salt,
  d—a composition comprising at least one soluble salt of an anion capable of forming an insoluble calcium salt.

In one embodiment, the kit also comprises an additional composition comprising at least one base.

In one embodiment, a second base may be added to compositions b, c or d.

Some of these compositions may be combined before the formation of the coprecipitate in order to reduce the number of vials.

In one embodiment, the composition comprising the osteogenic protein may also comprise the polysaccharide for forming the complex.

The composition comprising the osteogenic protein or the composition comprising the complex may also comprise the soluble salt of an anion capable of forming an insoluble calcium salt and/or a base.

In one embodiment, the composition comprising the polysaccharide may also comprise the soluble salt of an anion capable of forming an insoluble calcium salt and/or a base.

In one embodiment, the composition comprising the soluble calcium salt may also comprise a base.

In one embodiment, the kit comprises:
  a—a composition comprising at least one osteogenic protein,
  b—a composition comprising at least one anionic polysaccharide and at least one soluble salt of an anion capable of forming an insoluble calcium salt,
  c—a composition comprising at least one soluble calcium salt,
  d—a composition comprising at least one base.

In this embodiment, a second base, which may be identical to or different than the base of composition d, may be added to compositions b and c.

In one embodiment, the kit comprises
  a—a composition comprising at least one osteogenic protein,
  b—a composition comprising at least one anionic polysaccharide,
  c—a composition comprising at least one soluble calcium salt and at least one base,
  d—a composition comprising at least one soluble salt of an anion capable of forming an insoluble calcium salt.

In this embodiment, a second base, which may be identical to or different than the base of composition c, may be added to compositions b and d.

In one embodiment, the kit comprises:
  a—a composition comprising at least one osteogenic protein, b—a composition comprising at least one anionic polysaccharide and at least one base,
c—a composition comprising at least one soluble calcium salt,
d—a composition comprising at least one soluble salt of an anion capable of forming an insoluble calcium salt.

In this embodiment, a second base that is identical to or different from the base of composition b may be added to compositions c and d.

In one embodiment, the kit comprises
a—a composition comprising at least one osteogenic protein and at least one soluble salt of an anion capable of forming an insoluble calcium salt,
b—a composition comprising at least one anionic polysaccharide,
c—a composition comprising at least one soluble calcium salt,
d—a composition comprising at least one base.

In this embodiment, a second base, which may be identical to or different than the base of composition d, may be added to compositions b and c.

In one embodiment, the kit comprises
a—a composition comprising at least one osteogenic protein,
b—a composition comprising at least one anionic polysaccharide,
c—a composition comprising at least one soluble calcium salt,
d—a composition comprising at least one soluble salt of an anion capable of forming an insoluble calcium salt and at least one base.

In this embodiment, a second base, which may be identical to or different than the base of composition d, may be added to compositions b and c.

In one embodiment, the kit comprises
a—a composition comprising at least one osteogenic protein,
b—a composition comprising at least one anionic polysaccharide and at least one soluble salt of an anion capable of forming an insoluble calcium salt,
c—a composition comprising at least one soluble calcium salt,
d—a composition comprising at least one base.

In this embodiment, a second base, which may be identical to or different than the base of composition d, may be added to compositions b and c.

In one embodiment, the kit comprises:
a—a composition comprising at least one osteogenic protein,
b—a composition comprising at least one anionic polysaccharide, at least one base and at least one soluble salt of an anion capable of forming an insoluble calcium salt,
c—a composition comprising at least one soluble calcium salt.

In one embodiment, the kit comprises:
a—a composition comprising at least one osteogenic protein/anionic polysaccharide complex and at least one soluble salt of an anion capable of forming an insoluble calcium salt,
b—a composition comprising at least one soluble calcium salt,
c—a composition comprising at least one base.

In this embodiment, a second base that is identical to or different from the base of composition c may be added to the other compositions.

In one embodiment, the kit comprises:
a—a composition comprising at least one osteogenic protein,
b—a composition comprising at least one anionic polysaccharide and at least one soluble salt of an anion capable of forming an insoluble calcium salt,
c—a composition comprising at least one soluble calcium salt and at least one base.

In this embodiment, a second base that is identical to or different from the base of composition c may be added to composition b.

In one embodiment, the kit comprises:
a—a composition comprising at least one osteogenic protein,
b—a composition comprising at least one anionic polysaccharide and at least one soluble salt of an anion capable of forming an insoluble calcium salt,
c—a composition comprising at least one soluble calcium salt.

In one embodiment, the kit comprises:
a—a composition comprising at least one osteogenic protein/anionic polysaccharide complex,
b—a composition comprising at least one soluble calcium salt and at least one base,
c—a composition comprising at least one soluble salt of an anion capable of forming an insoluble calcium salt.

In this embodiment, a second base that is identical to or different from the base of composition b may be added to the other compositions.

In one embodiment, the kit comprises:
a—a composition comprising at least one osteogenic protein/anionic polysaccharide complex,
b—a composition comprising at least one soluble calcium salt,
c—a composition comprising at least one soluble salt of an anion capable of forming an insoluble calcium salt.

In one embodiment, the kit comprises:
a—a composition comprising at least one osteogenic protein/anionic polysaccharide complex,
b—a composition comprising at least one soluble calcium salt,
c—a composition comprising at least one soluble salt of an anion capable of forming an insoluble calcium salt and at least one base.

In this embodiment, a second base that is identical to or different from the base of composition c may be added to the other compositions.

In one embodiment, the kit comprises:
a—a composition comprising at least one osteogenic protein/anionic polysaccharide complex and at least one soluble salt of an anion capable of forming an insoluble calcium salt,
b—a composition comprising at least one soluble calcium salt.

In one embodiment, the kit comprises:
a—a composition comprising at least one osteogenic protein/anionic polysaccharide complex and at least one soluble salt of an anion capable of forming an insoluble calcium salt,
b—a composition comprising at least one soluble calcium salt and at least one base.

In one embodiment, the kit comprises:
a—a composition comprising at least one osteogenic protein/anionic polysaccharide complex and at least one soluble salt of an anion capable of forming an insoluble calcium salt and at least one base,
b—a composition comprising at least one soluble calcium salt.

In one embodiment, the kit comprises:
a—a composition comprising at least one osteogenic protein/anionic polysaccharide complex and at least one soluble salt of an anion capable of forming an insoluble calcium salt and at least one base,
b—a composition comprising at least one soluble calcium salt and at least one base.

In one embodiment, the composition comprising at least one osteogenic protein also comprises at least one growth factor with chemo-attracting and angiogenic power.

In one embodiment, the kit also comprises at least one organic matrix or a mineral matrix or a mixed matrix.

In one embodiment, the compositions constituting the kit are aqueous solutions.

In one embodiment, the compositions constituting the kit are lyophilizates.

In one embodiment, some of the compositions constituting the kit are lyophilizates.

In this embodiment, the lyophilizates are rehydrated before reaction, with water or one of the other compositions in solution.

Thus, for example, the composition comprising the osteogenic protein in lyophilizate form may be rehydrated with the solution comprising an anionic polysaccharide, or with the solution comprising an anionic polysaccharide and a soluble salt of an anion capable of forming an insoluble calcium salt and/or a base.

In one embodiment, the formulations, medical devices and pharmaceutical products comprising said precipitate are aqueous suspensions.

In one embodiment, the pharmaceutical formulations and products comprising said precipitate are lyophilizates.

In this embodiment, the lyophilizates are rehydrated before use, with physiological saline or blood.

The term "osteogenic protein" means an osteogenic growth factor or BMP, alone or in combination with a BMP chosen from the group of therapeutically active BMPs (Bone Morphogenetic Proteins).

More particularly, the osteogenic proteins are chosen from the group consisting of BMP-2 (dibotermine-alpha), BMP-4, BMP-7 (eptotermine-alpha), BMP-14 and GDF-5, alone or in combination.

The BMPs used are recombinant human BMPs, obtained according to the techniques known to those skilled in the art or purchased from suppliers, for instance the company Research Diagnostic Inc. (USA).

The term "growth factor with chemo-attracting and angiogenic power" means proteins such as PDGF, especially PDGF-BB, VEGF or FGF, especially FGF-2.

In one embodiment, the osteogenic protein is chosen from the group consisting of BMP-2 (dibotermine-alpha), BMP-4, BMP-7 (eptotermine-alpha), BMP-14 and GDF-5, alone or in combination, and the at least one growth factor with chemo-attracting and angiogenic power is PDGF.

In one embodiment, the composition comprises at least BMP-2 and PDGF-BB.

In one embodiment, the composition comprises at least BMP-7 and PDGF-BB.

In one embodiment, the composition comprises at least GDF-5 and PDGF-BB.

In one embodiment, the osteogenic protein is chosen from the group consisting of BMP-2 (dibotermine-alpha), BMP-4, BMP-7 (eptotermine-alpha), BMP-14 and GDF-5, alone or in combination, and the at least one growth factor with chemo-attracting and angiogenic power is VEGF.

In one embodiment, the osteogenic protein is chosen from the group consisting of BMP-2 (dibotermine-alpha), BMP-4, BMP-7 (eptotermine-alpha), BMP-14 and GDF-5, alone or in combination, and the at least one growth factor with chemo-attracting and angiogenic power is FGF.

The soluble calcium salt is a calcium salt whose anion is chosen from the group consisting of chloride, D-gluconate, formate, D-saccharate, acetate, L-lactate, glutamate and aspartate.

In one embodiment, the soluble calcium salt is calcium chloride.

The term "soluble salt of an anion capable of forming a precipitate with the calcium ion" means a soluble salt whose anion is chosen from the group consisting of phosphate anions comprising the phosphate ion $PO_4^{3-}$, the hydrogen phosphate ion $HPO_4^{2-}$ and the dihydrogen phosphate ion $H_2PO_4^{-}$.

In one embodiment, a second anion chosen from the group consisting of oxalate, ascorbate, carbonate and sulfate anions is also added to the composition comprising a phosphate anion.

The soluble salts of an anion that can form a precipitate with the calcium ion are chosen from the group consisting of sodium phosphates, sodium oxalate, sodium ascorbate, sodium carbonate, sodium sulfate and sodium hydrogen carbonate.

The term "anionic polysaccharide" means a polysaccharide chosen from the group of polysaccharides functionalized with hydrophobic derivatives.

In one embodiment, the polysaccharides are chosen from the group of polysaccharide derivatives predominantly comprising glycoside bonds of (1,4) and/or (1,3) and/or (1,2) type, functionalized with at least one tryptophan derivative as described in patent application FR 08/55567.

These polysaccharides are mainly consisted of glycoside bonds of (1,4) and/or (1,3) and/or (1,2) type. They may be neutral, i.e. not bearing acid or anionic functions and bearing acid functions.

They are functionalized with at least one tryptophan derivative, noted Trp:
said tryptophan derivative being grafted or linked to the polysaccharides by coupling with an acid function, said acid function possibly being an acid function of an anionic polysaccharide and/or an acid function borne by a linker R linked to the polysaccharide via a function F, said function F resulting from coupling between the linker R and an —OH function of the neutral or anionic polysaccharide, F being either an ester, thioester, amide, carbonate, carbamate, ether, thioether or amine function, R being a chain comprising between 1 and 18 carbons, optionally branched and/or unsaturated, comprising one or more heteroatoms, such as O, N and/or S, and having at least one acid function, Trp being a residue of a tryptophan derivative, L or D, produced by coupling between the amine of tryptophan and the at least one acid borne by the group R and/or an acid borne by the anionic polysaccharide.

According to the invention, the polysaccharide predominantly comprising glycoside bonds of (1,4), (1,3) and/or (1,2)

type, functionalized with at least one tryptophan derivative, may correspond to the general formula I below:

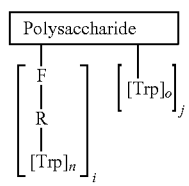

Formula I the polysaccharide being consisted mainly of glycoside bonds of (1,4) and/or (1,3) and/or (1,2) type,
F resulting from coupling between the linker R and an —OH function of the neutral or anionic polysaccharide, being either an ester, thioester, amide, carbonate, carbamate, ether, thioether or amine function,
R being a chain comprising between 1 and 18 carbons, optionally branched and/or unsaturated, comprising one or more heteroatoms, such as O, N and/or S, and having at least one acid function,
Trp being a residue of a tryptophan derivative, L or D, produced by coupling between the amine of the tryptophan derivative and the at least one acid borne by the group R and/or an acid borne by the anionic polysaccharide,
n represents the mole fraction of the groups R substituted with Trp and is between 0.05 and 0.7,
o represents the mole fraction of the acid functions of the polysaccharides that are substituted with Trp and is between 0.05 and 0.7,
i represents the mole fraction of acid functions borne by the group R per saccharide unit and is between 0 and 2,
j represents the mole fraction of acid functions borne by the anionic polysaccharide per saccharide unit and is between 0 and 1,
(i+j) represents the mole fraction of acid functions per saccharide unit and is between 0.1 and 2,
when R is not substituted with Trp, then the acid(s) of the group R are carboxylates of a cation, preferably of an alkali metal such as Na or K,
when the polysaccharide is an anionic polysaccharide, when one or more acid functions of the polysaccharide are not substituted with Trp, then they are salified with a cation, preferably an alkali metal cation such as Na$^+$ or K$^+$,
said polysaccharides being amphiphilic at neutral pH.

In one embodiment, F is either an ester, a carbonate, a carbamate or an ether.

In one embodiment, the polysaccharide is predominantly consisted of glycoside bonds of (1,4) type.

In one embodiment, the polysaccharide predominantly consisted of glycoside bonds of (1,4) type is chosen from the group consisting of pullulan, alginate, hyaluronan, xylan, galacturonan or a water-soluble cellulose.

In one embodiment, the polysaccharide is a pullulan.
In one embodiment, the polysaccharide is an alginate.
In one embodiment, the polysaccharide is a hyaluronan.
In one embodiment, the polysaccharide is a xylan.
In one embodiment, the polysaccharide is a galacturonan.
In one embodiment, the polysaccharide is a water-soluble cellulose.
In one embodiment, the polysaccharide is predominantly consisted of glycoside bonds of (1,3) type.

In one embodiment, the polysaccharide predominantly consisted of glycoside bonds of (1,3) type is a curdlan.

In one embodiment, the polysaccharide is predominantly consisted of glycoside bonds of (1,2) type.

In one embodiment, the polysaccharide predominantly consisted of glycoside bonds of (1,2) type is an inulin.

In one embodiment, the polysaccharide is predominantly consisted of glycoside bonds of (1,4) and (1,3) type.

In one embodiment, the polysaccharide predominantly consisted of glycoside bonds of (1,4) and (1,3) type is a glucan.

In one embodiment, the polysaccharide is predominantly consisted of glycoside bonds of (1,4) and (1,3) and (1,2) type.

In one embodiment, the polysaccharide predominantly consisted of glycoside bonds of (1,4) and (1,3) and (1,2) type is mannan.

In one embodiment, the polysaccharide according to the invention is characterized in that the group R is chosen from the following groups:

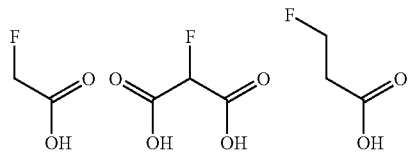

or salts thereof of alkali metal cations.

In one embodiment, the polysaccharide according to the invention is characterized in that the tryptophan derivative is chosen from the group consisting of tryptophan, tryptophanol, tryptophanamide and 2-indolethylamine, and the salts thereof of an alkali metal cation.

In one embodiment, the polysaccharide according to the invention is characterized in that the tryptophan derivative is chosen from the tryptophan esters of formula II:

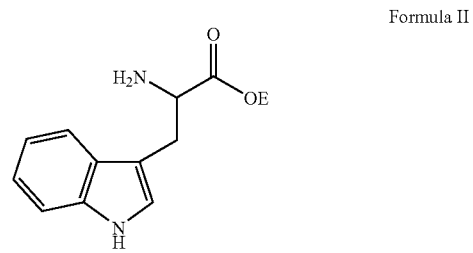

Formula II

E being a group, which may be:
a linear or branched $C_1$ to $C_8$ alkyl,
a linear or branched $C_6$ to $C_{20}$ alkylaryl or arylalkyl.

The polysaccharide may have a degree of polymerization m of between 10 and 10 000.

In one embodiment, it has a degree of polymerization m of between 10 and 1000.

In another embodiment, it has a degree of polymerization m of between 10 and 500.

In one embodiment, the polysaccharides are chosen from the group of dextrans functionalized with hydrophobic amino acids such as tryptophan and tryptophan derivatives as described in patent application FR 07/02316.

According to the invention, the functionalized dextran may correspond to the general formula III below:

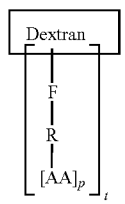

Formula III

R being a chain comprising between 1 and 18 carbons, optionally branched and/or unsaturated, comprising one or more heteroatoms, such as O, N and/or S, and having at least one acid function, F resulting from coupling between the linker R and an —OH function of the neutral or anionic polysaccharide, being either an ester, thioester, amide, carbonate, carbamate, ether, thioether or amine function, AA being a hydrophobic amino acid residue, L or D, produced by coupling between the amine of the amino acid and an acid borne by the group R, t represents the mole fraction of the substituent F—R—[AA]n per glycoside unit, and is between 0.1 and 2, p represents the mole fraction of groups R substituted with AA and is between 0.05 and 1, and when R is not substituted with AA, then the acid(s) of the group R are carboxylates of a cation, preferably of an alkali metal cation such as $Na^+$, $K^+$, said dextran being amphiphilic at neutral pH.

In one embodiment, the alkali metal cation is $Na^+$.

In one embodiment, F is either an ester, a carbonate, a carbamate or an ether.

In one embodiment, the polysaccharide according to the invention is a carboxymethyl dextran of formula IV.

Formula IV

R = H

R = * or the corresponding acid.

In one embodiment, the polysaccharide according to the invention is a monosuccinic ester of dextran of formula V:

Formula V

R = H

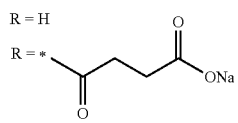

or the corresponding acid.

In one embodiment, the polysaccharide according to the invention is characterized in that the group R is chosen from the following groups:

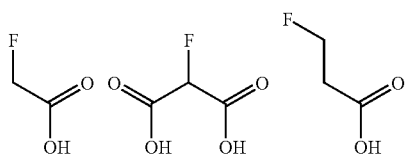

or the salts thereof of alkali metal cations.

In one embodiment, the dextran according to the invention is characterized in that the hydrophobic amino acid is chosen from tryptophan derivatives, such as tryptophan, tryptophanol, tryptophanamide or 2-indolethylamine, and salts thereof of an alkali metal cation.

In one embodiment, the dextran according to the invention is characterized in that the tryptophan derivatives are chosen from tryptophan esters of formula II as defined previously.

In one embodiment, the dextran according to the invention is a carboxymethyl dextran modified with tryptophan, of formula VI:

Formula VI

R = H

R = *

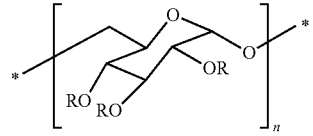

R =

In one embodiment, the dextran according to the invention is a monosuccinic ester of dextran modified with tryptophan, of formula VII:

Formula VII

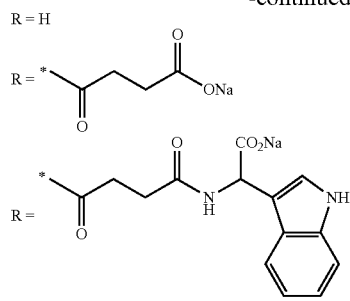

In one embodiment, the dextran according to the invention is characterized in that the hydrophobic amino acid is chosen from phenylalanine, leucine, isoleucine and valine, and alcohol, amide or decarboxylated derivatives thereof.

In one embodiment, the dextran according to the invention is characterized in that the phenylalanine, leucine, isoleucine and valine derivatives are chosen from the esters of these amino acids, of formula VIII:

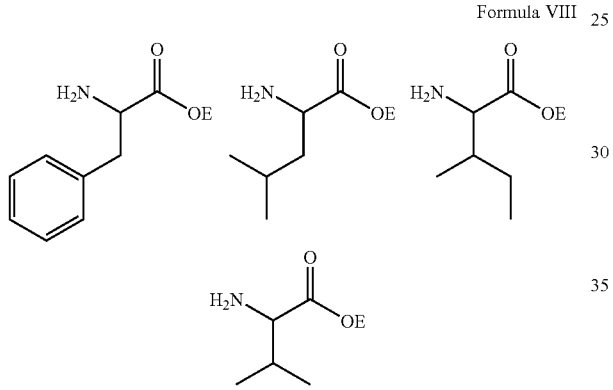

Formula VIII

E being as defined previously.

In one embodiment, the dextran according to the invention is characterized in that the hydrophobic amino acid is phenylalanine, and alcohol, amide or decarboxylated derivatives thereof.

The dextran may have a degree of polymerization m of between 10 and 10 000.

In one embodiment, it has a degree of polymerization m of between 10 and 1000.

In another embodiment, it has a degree of polymerization m of between 10 and 500.

In one embodiment, the polysaccharides are chosen from the group of polysaccharides comprising carboxyl functional groups such as those described in patent application FR 08/05506, at least one of which is substituted with a hydrophobic alcohol derivative, noted Ah:

said hydrophobic alcohol (Ah) being grafted or linked to the anionic polysaccharide via a coupling arm R, the said coupling arm being linked to the anionic polysaccharide via a function F', the said function F' resulting from coupling between the amine function of the linker R and a carboxyl function of the anionic polysaccharide, and the said coupling arm being linked to the hydrophobic alcohol via a function G resulting from coupling between a carboxyl, isocyanate, thio acid or alcohol function of the coupling arm and a function of the hydrophobic alcohol, the carboxyl functions of the anionic polysaccharide that are unsubstituted being in the form of carboxylate of a cation, preferably of an alkali metal cation such as $Na^+$ or K.

F' being an amide function,

G being either an ester, thioester, carbonate or carbamate function,

R being a chain comprising between 1 and 18 carbons, optionally branched and/or unsaturated, optionally comprising one or more heteroatoms, such as O, N and/or S, and having at least one acid function, Ah being a residue of a hydrophobic alcohol, produced by coupling between the hydroxyl function of the hydrophobic alcohol and at least one electrophilic function borne by the group R, the said polysaccharide comprising carboxyl functional groups being amphiphilic at neutral pH.

The polysaccharide comprising carboxyl functional groups partly substituted with hydrophobic alcohols is chosen from polysaccharides comprising carboxyl functional groups of general formula IX:

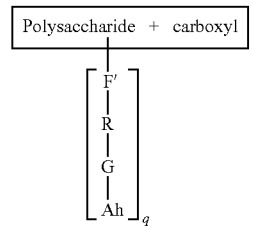

Formula IX in which q represents the mole fraction of carboxyl functions of the polysaccharide that are substituted with F—R-G-Ah and is between 0.01 and 0.7, F', R, G and Ah corresponding to the definitions given above, and when the carboxyl function of the polysaccharide is not substituted with F'—R-G-Ah, then the carboxyl functional group(s) of the polysaccharide are carboxylates of a cation, preferably of an alkali metal cation such as $Na^+$ or K.

In one embodiment, the polysaccharides comprising carboxyl functional groups are polysaccharides naturally bearing carboxyl functional groups and are chosen from the group consisting of alginate, hyaluronan and galacturonan.

In one embodiment, the polysaccharides comprising carboxyl functional groups are synthetic polysaccharides obtained from polysaccharides naturally comprising carboxyl functional groups or from neutral polysaccharides on which at least 15 carboxyl functional groups per 100 saccharide units have been grafted, of general formula X:

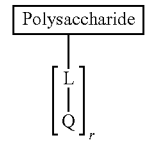

X the natural polysaccharides being chosen from the group of polysaccharides mainly consisted of glycoside bonds of (1,6) and/or (1,4) and/or (1,3) and/or (1,2) type, L being a bond resulting from coupling between the linker Q and an —OH function of the polysaccharide, and being either an ester, thioester, carbonate, carbamate or ether function, r represents the mole fraction of the substituents L-Q per saccharide unit of the polysaccharide, Q being a chain comprising between 1 and 18 carbons, optionally branched and/or unsaturated, comprising one or more heteroatoms, such as O, N and/or S, and comprising at least one carboxyl functional group, —$CO_2H$.

In one embodiment, the polysaccharide is mainly consisted of glycoside bonds of (1,6) type.

In one embodiment, the polysaccharide mainly consisted of glycoside bonds of (1,6) type is dextran.

In one embodiment, the polysaccharide is mainly consisted of glycoside bonds of (1,4) type.

In one embodiment, the polysaccharide mainly consisted of glycoside bonds of (1,4) type is chosen from the group consisting of pullulan, alginate, hyaluronan, xylan, galacturonan or a water-soluble cellulose.

In one embodiment, the polysaccharide is a pullulan.
In one embodiment, the polysaccharide is an alginate.
In one embodiment, the polysaccharide is a hyaluronan.
In one embodiment, the polysaccharide is a xylan.
In one embodiment, the polysaccharide is a galacturonan.
In one embodiment, the polysaccharide is a water-soluble cellulose.

In one embodiment, the polysaccharide is mainly consisted of glycoside bonds of (1,3) type.

In one embodiment, the polysaccharide mainly consisted of glycoside bonds of (1,3) type is a curdlan.

In one embodiment, the polysaccharide is mainly consisted of glycoside bonds of (1,2) type.

In one embodiment, the polysaccharide mainly consisted of glycoside bonds of (1,2) type is an inulin.

In one embodiment, the polysaccharide is mainly consisted of glycoside bonds of (1,4) and (1,3) type.

In one embodiment, the polysaccharide mainly consisted of glycoside bonds of (1,4) and (1,3) type is a glucan.

In one embodiment, the polysaccharide is mainly consisted of glycoside bonds of (1,4) and (1,3) and (1,2) type.

In one embodiment, the polysaccharide mainly consisted of glycoside bonds of (1,4) and (1,3) and (1,2) type is mannan.

In one embodiment, the polysaccharide according to the invention is characterized in that the group Q is chosen from the following groups:

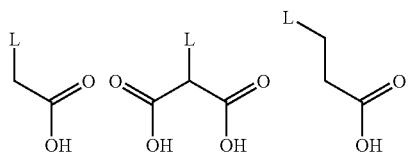

In one embodiment, r is between 0.1 and 2.
In one embodiment, r is between 0.2 and 1.5.
In one embodiment, the group R according to the invention is characterized in that it is chosen from amino acids.

In one embodiment, the amino acids are chosen from α-amino acids.

In one embodiment, the α-amino acids are chosen from natural α-amino acids.

In one embodiment, the natural α-amino acids are chosen from leucine, alanine, isoleucine, glycine, phenylalanine, tryptophan and valine.

In one embodiment, the hydrophobic alcohol is chosen from fatty alcohols.

In one embodiment, the hydrophobic alcohol is chosen from alcohols consisted of a saturated or unsaturated alkyl chain comprising from 4 to 18 carbons.

In one embodiment, the fatty alcohol is chosen from myristyl alcohol, cetyl alcohol, stearyl alcohol, cetearyl alcohol, butyl alcohol, oleyl alcohol and lanolin.

In one embodiment, the hydrophobic alcohol is chosen from cholesterol derivatives.

In one embodiment, the cholesterol derivative is cholesterol.

In one embodiment, the hydrophobic alcohol Ah is chosen from tocopherols.

In one embodiment, the tocopherol is α-tocopherol.
In one embodiment, the α-tocopherol is racemic α-tocopherol.

In one embodiment, the hydrophobic alcohol is chosen from alcohols bearing an aryl group.

In one embodiment, the alcohol bearing an aryl group is chosen from benzyl alcohol and phenethyl alcohol.

The polysaccharide may have a degree of polymerization m of between 10 and 10 000.

In one embodiment, it has a degree of polymerization m of between 10 and 1000.

In another embodiment, it has a degree of polymerization m of between 10 and 500.

In one embodiment, the polysaccharide is chosen from the group consisting of dextran functionalized with tryptophan, dextran functionalized with octanol phenylalaninate, dextran functionalized with octanol glycinate, dextran functionalized with dodecanol glycinate or dextran functionalized with tryptophan ethyl ester.

In order to neutralize the acidic compounds present in the mixture, the bases are chosen from mineral or organic bases.

Among the mineral bases, mention will be made of sodium hydroxide, sodium hydrogen carbonate and sodium carbonate.

Among the organic bases, mention will be made of amines and deprotonated amino acids.

Among the organic bases, mention will be made of imidazole and derivatives thereof, especially histidine, proline, ethanolamine and serine.

In one embodiment, an organic matrix may be used in order to promote repair; it is chosen from matrices based on purified, sterilized and crosslinked natural collagen.

Natural polymers such as collagen are components of the extracellular matrix that promote cell attachment, migration and differentiation. They have the advantage of being extremely biocompatible and are degraded by enzymatic digestion mechanisms. Collagen-based matrices are obtained from fibrillar collagen of type I or IV extracted from bovine or porcine tendon or bone. These collagens are first purified, before being crosslinked and then sterilized.

They may also be obtained by resorption in acidic medium of autologous bone, leading to the loss of most of the mineralized components, but to preservation of the collagen or non-collagen proteins, including growth factors. These demineralized matrices may also be prepared in inactive form after extraction with chaotropic agents. These matrices are essentially composed of insoluble and crosslinked collagen of type I.

Mixed materials may also be used, for example a matrix that combines collagen and inorganic particles. These materials may be in the form of a composite material with reinforced mechanical properties or in the form of a "putty" in which the collagen acts as a binder.

The inorganic materials that may be used essentially comprise calcium phosphate-based ceramics such as hydroxyapatite (HA), tricalcium phosphate (TCP), biphasic calcium phosphate (BCP) or amorphous calcium phosphate (ACP), the main value of which is that they have a chemical composition very similar to that of bone. These materials have good mechanical properties and are immunologically inert. These materials may be in various forms, such as powders, granulates or blocks. These materials have very different degradation rates as a function of their composition. Thus, hydroxyapatite degrades very slowly (several months), whereas tricalcium phosphate degrades more quickly (several weeks). It is for this reason that biphasic calcium phosphates were developed, since they have intermediate resorption rates. These inorganic materials are known to be mainly osteoconducting.

In one embodiment, the organic matrix is a crosslinked hydrogel.

A crosslinked hydrogel is obtained by crosslinking polymer chains. The inter-chain covalent bonds define an organic matrix. The polymers that may be used to constitute an organic matrix are described in the review by Hoffman entitled Hydrogels for biomedical applications (Adv. Drug Deliv. Rev, 2002, 43, 3-12).

In one embodiment, the implant may comprise a non-crosslinked hydrogel.

The term "non-crosslinked hydrogel" means a hydrophilic three-dimensional polymer network capable of adsorbing a large amount of water or of biological liquids (Peppas et al., Eur. J. Pharm. Biopharm. 2000, 50, 27-46). This hydrogel is consisted of physical interactions and is therefore not obtained by chemical crosslinking of the polymer chains.

The list of polymers forming hydrogels is very long, and a large but not exhaustive list is given in the review by Hoffman entitled Hydrogels for biomedical applications (Adv. Drug Deliv. Rev., 2002, 43, 3-12). Among these polymers are synthetic polymers and natural polymers. Another review covering polysaccharides that form hydrogels makes it possible to choose a polymer that is useful for the invention (Alhaique et al. J. Control. Release, 2007, 119, 5-24).

In one embodiment, the polymer forming a hydrogel is chosen from the group of synthetic polymers, including copolymers of ethylene glycol and of lactic acid, copolymers of ethylene glycol and of glycolic acid, poly(N-vinylpyrrolidone), polyvinylic acids, polyacrylamides and polyacrylic acids.

In one embodiment, the polymer forming a hydrogel is chosen from the group of natural polymers, including hyaluronic acid, keratan, pullulan, pectin, dextran, cellulose and cellulose derivatives, alginic acid, xanthan, carrageenan, chitosan, chondroitin, collagen, gelatin, polylysine, fibrin and biologically acceptable salts thereof.

In one embodiment, the natural polymer is chosen from the group of polysaccharides forming hydrogels, including hyaluronic acid, alginic acid, dextran, pectin, cellulose and derivatives thereof, pullulan, xanthan, carrageenan, chitosan, chondroitin, and biologically acceptable salts thereof.

In one embodiment, the natural polymer is chosen from the group of polysaccharides forming hydrogels, including hyaluronic acid, alginic acid, and biologically acceptable salts thereof.

In one embodiment, the hydrogel may be prepared just before implanting or injecting.

In one embodiment, the hydrogel may be prepared and stored in a prefilled syringe in order then to be implanted or injected.

In one embodiment, the hydrogel may be prepared by rehydration of a lyophilizate just before implanting or injecting, or may be implanted in dehydrated form.

Among the various matrices which can be used, mention will be made, by way of example, of collagen sponges such as Helistat® (Integra LifeSciences, Plainsboro, N.J.), DBMs (Demineralized Bone Matrix) alone or as a mixture with other organic materials such as polysaccharides, glycerol or gelatins such as Osteofil® (Medtronic), Allomatrix® (Wright), Grafton® (Osteotech), DBX® (MTF/Synthes), Bioset® (Regeneration Technologies), matrices consisting of mineral phases such as Vitoss®(Orthivista), Osteoset® (Wright) or mixed matrices such as MasterGraft® (Medtronic), Healos® (Depuy Spine), CopiOs® (Zimmer), Sunnmax Collagen Bone Graft Matrix (Sunmax).

The system after formation of the coprecipitate is consisted of two phases, a liquid phase and a solid phase.

In the rest of the specification, when the notion of volume is employed, it is the total volume comprising the two phases.

The amounts per unit volume in the product resulting after mixing together the compositions of the various forms of the kit are given below and do not comprise the amounts of calcium ions or phosphate ions originating from the matrix when the mixed or mineral matrices are used.

In one embodiment, the total amounts of the various proteins per unit volume are between 0.01 mg and 2 mg, preferably between 0.05 mg and 1.5 mg and more preferably between 0.1 mg and 1.5 mg per ml of suspension obtained.

The total amounts of phosphates per unit volume are between 0.02 mmol and 0.5 mmol and preferably between 0.05 and 0.25 mmol per ml of suspension obtained.

The total amounts of calcium per unit volume are between 0.01 mmol and 1 mmol, preferably between 0.05 and 1 mmol and more preferably between 0.1 mmol and 0.5 mmol per unit volume.

The percentage of calcium ions in the solid phase is between 60% and 95% of the calcium ions introduced.

The total amounts of polysaccharides per unit volume are between 1 and 100 mg, preferably between 2 and 40 mg per ml of suspension obtained. The percentage of polysaccharides in the solid phase is greater than 80% of the polysaccharide introduced.

The amounts of base used correspond to about 0.1 to 2 equivalents relative to the protons provided by the phosphate ions.

As a function of volumes used and of the number of compositions, the amounts used in the starting compositions may be determined by calculation. This may be performed for the various embodiments of the kits.

In one embodiment, for a vertebral implant, the doses of osteogenic growth factor will be between 0.01 mg and 20 mg, preferably between 0.05 mg and 8 mg, preferably between 0.1 mg and 4 mg and more preferably between 0.1 mg and 2 mg, whereas the doses commonly accepted in the literature are between 8 and 12 mg.

In one embodiment, for a vertebral implant, the doses of angiogenic growth factor will be between 0.05 mg and 8 mg, preferably between 0.1 mg and 4 mg and more preferably between 0.1 mg and 2 mg.

In one embodiment, for the formulation of an implant comprising the coprecipitate according to the invention, a kit comprising three vials is prepared, said vials containing:

in the first, between 2 and 10 mg of osteogenic protein in lyophilized form, in the second, between 2 and 6 ml of a solution of a polysaccharide at a concentration of between 10 and 50 mg/ml and of an equimolar mixture of sodium hydrogen phosphate $Na_2HPO_4$ and of sodium dihydrogen phosphate $NaH_2PO_4$ with a concentration of between 0.15 and 0.50 M, in the third, between 2 and 6 ml of a calcium chloride solution at a concentration of between 0.25 and 0.90 M.

In one embodiment, the second vial also contains a sodium bicarbonate solution at a concentration of between 0.05 and 0.8 M.

In one embodiment, the second and third vials also contain a histidine solution at a concentration of between 0.02 and 0.2 M.

In one embodiment, the third vial also contains a proline solution at a concentration of between 0.05 and 0.3 M.

The solutions are added simultaneously or successively before implanting, to a collagen sponge with a volume of between 15 and 30 ml.

In one embodiment, for the formulation of an implant comprising the coprecipitate according to the invention, three solutions are mixed together, comprising:

in the first, a volume of between 1 and 3 ml containing an osteogenic protein at a concentration of between 0.33 and 2 mg/ml, in the second, a volume of between 1 and 3 ml containing a polysaccharide at a concentration of between 5 and 15 mg/ml and an equimolar mixture of sodium hydrogen phosphate $Na_2HPO_4$ and of sodium dihydrogen phosphate $NaH_2PO_4$ with a concentration of between 0.05 and 0.15 M, in the third, a volume of between 1 and 3 ml containing calcium chloride at a concentration of between 0.25 and 0.50 M.

In one embodiment, a sodium bicarbonate solution at a concentration of between 0.20 and 0.4 M is added to the mixture obtained.

In one embodiment, a histidine solution at a concentration of between 0.02 and 0.15 M is added to the mixture obtained.

In one embodiment, a proline solution at a concentration of between 0.05 and 0.3 M is added to the mixture obtained.

The mixture comprising the coprecipitate according to the invention is then lyophilized.

At the time of use, it is rehydrated with injectable water and/or blood to about 35% of the initial volume.

The invention also relates to the use of the compositions of the invention by implantation, for example, for filling bone defects, for performing vertebral fusions or maxillo-facial repairs, or for treating bone fractures, in particular of the pseudarthrosis type.

The invention also relates to the use of the compositions of the invention by injection for the treatment of bone defects, especially those caused by osteoporosis, and for any other pathology which can be treated percutaneously.

The invention also relates to the use of the compositions according to the invention as bone implants.

In one embodiment, the compositions may be used in combination with a prosthetic device of the vertebral prosthesis or vertebral fusion cage type.

The invention also relates to therapeutic and surgical methods using the compositions in bone reconstruction.

In these various therapeutic uses, the size of the matrix and the amount of osteogenic growth factor depend on the volume of the site to be treated.

Examples of various embodiments of the invention are given hereinbelow.

Examples of kits are given as non-limiting guides.

EXAMPLE 1

Preparation of a Kit Containing 5 Vials

Kit 1: A kit of 5 vials comprises a vial containing osteogenic protein in lyophilized or solution form, a vial containing a polymer in lyophilized or solution form, a vial containing a soluble calcium salt in lyophilized or solution form, a vial containing a soluble phosphate salt in lyophilized or solution form and a vial containing a base in lyophilized or solution form.

EXAMPLE 2

Preparation of a Kit Containing 4 Vials

Kit 2: A kit of 4 vials comprises a vial containing osteogenic protein in lyophilized or solution form, a vial containing a polymer in lyophilized or solution form, a vial containing a soluble calcium salt in lyophilized or solution form and a vial containing a soluble phosphate salt in lyophilized or solution form.

EXAMPLE 3

Preparation of a Kit Containing 4 Vials

Kit 3: A kit of 4 vials comprises a vial containing osteogenic protein in lyophilized or solution form, a vial containing a polymer and a soluble phosphate salt in lyophilized or solution form, a vial containing a soluble calcium salt in lyophilized or solution form and a vial containing a base in lyophilized or solution form.

EXAMPLE 4

Preparation of a Kit Containing 4 Vials

Kit 4: A kit of 4 vials comprises a vial containing osteogenic protein in lyophilized or solution form, a vial containing a polymer in lyophilized or solution form, a vial containing a soluble calcium salt and a base in lyophilized or solution form and a vial containing a soluble phosphate salt in lyophilized or solution form.

EXAMPLE 5

Preparation of a Kit Containing 4 Vials

Kit 5: A kit of 4 vials comprises a vial containing the complex between the osteogenic protein and a polymer in lyophilized or solution form, a vial containing a soluble calcium salt in lyophilized or solution form, a vial containing a soluble phosphate salt in lyophilized or solution form and a vial containing a base in lyophilized or solution form.

EXAMPLE 6

Preparation of a Kit Containing 3 Vials

Kit 6: A kit of 3 vials comprises a vial containing osteogenic protein in lyophilized or solution form, a vial containing a polymer and a soluble phosphate salt in lyophilized or solution form, a vial containing a soluble calcium salt and a base in lyophilized or solution form.

EXAMPLE 7

Preparation of a Kit Containing 3 Vials

Kit 7: A kit of 3 vials comprises a vial containing osteogenic protein in lyophilized or solution form, a vial containing a polymer and a soluble phosphate salt in lyophilized or solution form, a vial containing a soluble calcium salt in lyophilized or solution form.

EXAMPLE 8

Preparation of a Kit Containing 3 Vials

Kit 8: A kit of 3 vials comprises a vial containing the complex between the osteogenic protein and a polymer in lyophilized or solution form, a vial containing a soluble phosphate salt in lyophilized or solution form, a vial containing a soluble calcium salt and a base in lyophilized or solution form.

EXAMPLE 9

Preparation of a Kit Containing 3 Vials

Kit 9: A kit of 3 vials comprises a vial containing the complex between the osteogenic protein and a polymer in lyophilized or solution form, a vial containing a soluble phosphate salt in lyophilized or solution form, and a vial containing a soluble calcium salt in lyophilized or solution form.

EXAMPLE 10

Preparation of a Kit Containing 2 Vials

Kit 10: A kit of 2 vials comprises a vial containing the complex between the osteogenic protein and a lyophilized polymer and a soluble phosphate salt in lyophilized or solution form, and a vial containing a soluble calcium salt in lyophilized or solution form.

EXAMPLE 11

Preparation of a Kit Containing 2 Vials

Kit 11: A kit of 2 vials comprises a vial containing the complex between the osteogenic protein and a lyophilized polymer and a soluble phosphate salt in lyophilized or solution form, and a vial containing a soluble calcium salt and a base in lyophilized or solution form.

Examples of synthesis of polymers are given as non-limiting indications.

EXAMPLE 12

Preparation of a Dextran Functionalized with Tryptophan

Polymer 1 is a sodium dextran methylcarboxylate modified with the sodium salt of L-tryptophan, obtained from a dextran with a weight-average molar mass of 40 kg/mol (Pharmacosmos) according to the process described in patent application FR 07/02316. The mole fraction of sodium methylcarboxylate, unmodified or modified with tryptophan, i.e. t in formula III of the present patent application, is 1.03. The mole fraction of sodium methylcarboxylate modified with tryptophan, i.e. p in formula III of the present patent application, is 0.36.

EXAMPLE 13

Preparation of a Dextran Functionalized with Octanol Phenylalaninate

Polymer 2 is a sodium dextran methylcarboxylate modified with the octanoic ester of L-phenylalanine, obtained from a dextran with a weight-average molar mass of 40 kg/mol (Pharmacosmos) according to the process described in patent application PCT/IB2009007054. The mole fraction of sodium methylcarboxylate, unmodified or modified with the octanoic ester of L-phenylalanine, i.e. r in formula X of the present patent application, is 1.11. The mole fraction of sodium methylcarboxylate modified with the octanoic ester of L-phenylalanine, i.e. q in formula IX of the present patent application, is 0.09.

The solution of polymer 2 at the end of production is 30.45 mg/mL.

EXAMPLE 14

Preparation of a Dextran Functionalized with Octanol Glycinate

Polymer 3 is a sodium dextran methylcarboxylate modified with the octanoic ester of L-glycine, obtained from a dextran with a weight-average molar mass of 40 kg/mol (Pharmacosmos) according to the process described in patent application FR 08/05506. The mole fraction of sodium methylcarboxylate, unmodified or modified with the octanoic ester of L-glycine, i.e. r in formula X of the present patent application, is 1.09. The mole fraction of sodium methylcarboxylate modified with the octanoic ester of L-glycine, i.e. q in formula IX of the present patent application, is 0.22.

EXAMPLE 15

Preparation of a Dextran Functionalized with Tryptophan

Polymer 4 is a sodium dextran methylcarboxylate modified with the sodium salt of L-tryptophan, obtained from a dextran with a weight-average molar mass of 70 kg/mol (Pharmacosmos) according to the process described in patent application FR 07/02316. The mole fraction of sodium methylcarboxylate, unmodified or modified with tryptophan, i.e. t in formula III of the present patent application, is 1.14. The mole fraction of sodium methylcarboxylate modified with tryptophan, i.e. p in formula III of the present patent application, is 0.41.

EXAMPLE 16

Preparation of a Dextran Functionalized with Octanol Phenylalaninate

Polymer 5 is a sodium dextran methylcarboxylate modified with the octanoic ester of L-phenylalanine obtained from a dextran with a weight-average molar mass of 40 kg/mol (Pharmacosmos) according to the process described in patent application FR 08/05506. The mole fraction of sodium methylcarboxylate, unmodified or modified with the octanoic ester of L-phenylalanine, i.e. r in formula X of the present patent application, is 1.12. The mole fraction of sodium methylcarboxylates modified with the octanoic ester of L-phenylalanine, i.e. q in formula IX of the present patent application, is 0.22.

EXAMPLE 17

Preparation of a Dextran Functionalized with Dodecanol Glycinate

Polymer 6 is a sodium dextran methylcarboxylate modified with the dodecanoic ester of L-glycine obtained from a dextran with a weight-average molar mass of 40 kg/mol (Pharmacosmos) according to the process described in patent application FR 08/05506. The mole fraction of sodium methylcarboxylate, unmodified or modified with the dodecanoic ester of L-phenylglycine, i.e. r in formula X of the present patent application, is 1.04. The mole fraction of sodium methylcarboxylates modified with the dodecanoic ester of L-glycine, i.e. q in formula IX of the present patent application, is 0.13.

EXAMPLE 18

Preparation of a Dextran Functionalized with the Ethyl Ester of Tryptophan

Polymer 7 is a sodium dextran methylcarboxylate modified with the ethyl ester of L-tryptophan obtained from a dextran with a weight-average molar mass of 40 kg/mol (Pharmacosmos) according to the process described in patent application FR 07/02316. The mole fraction of sodium methylcarboxylate unmodified or modified with the ethyl ester of tryptophan, i.e. t in formula III of the present patent application, is 1.09. The mole fraction of sodium methylcarboxylates modified with the ethyl ester of tryptophan, i.e. p in formula III of the present patent application, is 0.47.

EXAMPLE 19

Preparation of a Solution of a Dextran Functionalized with Tryptophan

A concentrated solution of polymer 1 is prepared by dissolving 9.13 g of lyophilizate of polymer 1 (water content of about 25%) in 35.24 g of water. The solution is stirred for 30 minutes. The concentration of polymer 1 is 162.9 mg/g, determined in the dry extract. The density is 1.08. The concentration of polymer 1 is thus 175.9 mg/mL.

EXAMPLE 20

Preparation of a Solution of a Dextran Functionalized with Octanol Phenylalaninate A solution of polymer 2 at 40 mg/g is prepared by dissolving 3.12 g of lyophilizate of polymer 2 (water content of 14%) in 64 g of water.

EXAMPLE 21

Preparation of a Solution of a Dextran functionalized with octanol glycinate

A solution of polymer 3 at 38 mg/g is prepared by dissolving 3.95 g of lyophilizate of polymer 3 (water content of 4%) in 100 g of water.

Examples of solutions or lyophilizates of osteogenic proteins are given as non-limiting guides.

EXAMPLE 22

Solution of rhBMP-2 in 1 mM HCl Buffer 10 mL of a 0.15 mg/ml solution of rhBMP-2 are prepared by adding 10 mL of a 1 mM HCl solution to 1.5 mg of lyophilized rhBMP-2. This solution is incubated for two hours at 4° C. and filtered aseptically on a 0.22 μm membrane.

EXAMPLE 23

Solution of rhBMP-2 in Infuse Buffer

1 L of InFUSE buffer is prepared by dissolving, in a 1 L graduated flask filled with 800 mL of water, 5 g of sucrose, 25 g of glycine, 3.72 g of glutamic acid, 0.11 g of sodium chloride and 0.11 g of polysorbate 80. The pH of this solution is then adjusted to 4.5 by adding 16.8 mL of 1 N sodium hydroxide. The graduated flask is finally filled to the graduation mark to obtain the Infuse buffer. 1 mL of a solution of rhBMP-2 at 1.5 mg/ml in the InFUSE buffer is prepared by adding 1 mL of buffer to 1.5 mg of lyophilized rhBMP-2. This solution is incubated for two hours at 4° C. and filtered aseptically through a 0.22 μm membrane.

The solution may also be lyophilized.

EXAMPLE 24

Solution of rhBMP-7 in a 10 mM HCl Buffer

A solution of rhBMP-7 at 3.8 mg/ml is prepared by adding 1 mL of a 1 mM HCl solution to 3.8 mg of lyophilized rhBMP-7. The pH of this solution is 2.2. This solution is incubated for 15 minutes at room temperature and is filtered aseptically on a 0.22 μm membrane.

EXAMPLE 25

Solution of rhBMP-7 in a pH 3.5 5% Lactose Buffer

A solution of rhBMP-7 at 3.8 mg/ml is prepared by adding 7.8 mL of a 5% lactose solution whose pH has been set at 3.5 by adding 1 M HCl to 30.3 mg of lyophilized rhBMP-7. The pH of this solution is 3.5. This solution is incubated for 15 minutes at room temperature and filtered aseptically on a 0.22 μm membrane.

EXAMPLE 26

Solution of rhGDF-5 in a 10 mM HCl Buffer 1 mL of an rhGDF-5 solution at 1.5 mg/ml is prepared by adding 1 mL of a 10 mM HCl solution to 1.5 mg of lyophilized rhGDF-5. This solution is incubated for two hours at 4° C. and filtered aseptically on a 0.22 μm membrane.

Examples of preparation of solutions of soluble phosphate salts are given as non-limiting guides.

EXAMPLE 27

Sodium Phosphate Solution

A 1 M sodium phosphate solution is prepared in a graduated flask from an equimolar mixture of anhydrous sodium hydrogen phosphate and sodium dihydrogen phosphate (Sigma). This solution is incubated for 30 minutes at room temperature and filtered aseptically on a 0.22 μm membrane.

More dilute sodium phosphate solutions are prepared from the stock solution described above.

Examples of preparation of solutions of soluble calcium salts are given as non-limiting guides.

EXAMPLE 28

2 M Calcium Chloride Solution

Solution 1: A 2 M calcium chloride solution is prepared in a graduated flask from anhydrous or dihydrated calcium chloride (Sigma). This solution is incubated for 30 minutes at room temperature and filtered aseptically on a 0.22 µm membrane.

EXAMPLE 29

0.75 M Calcium Chloride Solution

Solution 2: A 0.75 M calcium chloride solution is prepared by diluting the 2 M calcium chloride solution described in the preceding example. This solution is incubated for 30 minutes at room temperature and filtered aseptically on a 0.22 µm membrane.

EXAMPLE 30

0.75 M Calcium Acetate Solution

Solution 3: A 0.75 M calcium acetate solution is prepared in a graduated flask from calcium acetate (Sigma). This solution is incubated for 30 minutes at room temperature and filtered aseptically on a 0.22 µm membrane.

EXAMPLE 31

0.75 M Calcium Gluconate Solution

Solution 4: A 0.75 M calcium gluconate solution is prepared in a graduated flask from calcium gluconate (Sigma). This solution is incubated for 30 minutes at room temperature and filtered aseptically on a 0.22 µm membrane.

Examples of preparation of solutions of bases are given as non-limiting illustrations.

EXAMPLE 32

1 M Histidine Solution

Solution 5: A 1 M histidine solution is prepared in a 1 L graduated flask by dissolving 155.2 g of L-histidine (Sigma) in the volume of deionized water necessary to reach the graduation mark. This solution is incubated for 30 minutes at room temperature and filtered aseptically on a 0.22 µm membrane.

EXAMPLE 33

2 M Proline Solution

Solution 6: A 2 M proline solution is prepared in a 1 L graduated flask by adding 230.2 g of L-proline (Sigma), 200 mL of 10 N sodium hydroxide and the volume of deionized water necessary to reach the graduation mark. This solution is incubated for 30 minutes at room temperature and filtered aseptically on a 0.22 µm membrane.

EXAMPLE 34

2 M Serine Solution

Solution 7: A 2 M serine solution is prepared in a 1 L graduated flask by adding 210.2 g of L-serine (Sigma), 200 mL of 10 N sodium hydroxide and the volume of deionized water necessary to reach the graduation mark. This solution is incubated for 30 minutes at room temperature and filtered aseptically on a 0.22 µm membrane.

EXAMPLE 35

2 M Glycine Solution

Solution 8: A 2 M glycine solution is prepared in a 1 L graduated flask by adding 150.1 g of L-glycine (Sigma), 200 mL of 10 N sodium hydroxide and the volume of deionized water necessary to reach the graduation mark. This solution is incubated for 30 minutes at room temperature and filtered aseptically on a 0.22 µm membrane.

EXAMPLE 36

2 M Alanine Solution

Solution 9: A 2 M alanine solution is prepared in a 1 L graduated flask by adding 178.2 g of L-alanine (Sigma), 200 mL of 10 N sodium hydroxide and the volume of deionized water necessary to reach the graduation mark. This solution is incubated for 30 minutes at room temperature and filtered aseptically on a 0.22 µm membrane.

EXAMPLE 37

2 M Lysine Solution

Solution 10: A 2 M lysine solution is prepared in a 1 L graduated flask by adding 292.4 g of L-lysine (Sigma), 200 mL of 10 N sodium hydroxide and the volume of deionized water necessary to reach the graduation mark. This solution is incubated for 30 minutes at room temperature and filtered aseptically on a 0.22 µm membrane.

Solutions of lower concentration of these various bases are obtained by dilution either with water or with a solution of the calcium salts described previously.

EXAMPLE 38

Sodium Hydrogen Carbonate Solution

A 1.2 M sodium hydrogen carbonate solution is prepared in a graduated flask from anhydrous sodium hydrogen carbonate (Sigma). This solution is incubated for 30 minutes at room temperature and filtered aseptically on a 0.22 µm membrane.

More dilute sodium hydrogen carbonate solutions are prepared from the stock solution described above.

EXAMPLE 39

TRIS Solution

A 0.5 M solution of tris(hydroxymethyl)aminomethane is prepared in a graduated flask from ultrapure tris(hydroxymethyl)aminomethane (Sigma) and adjusted to pH 7.4 using 1 M hydrochloric acid. This solution is incubated for 30 minutes at room temperature and filtered aseptically on a 0.22 µm membrane.

Examples of preparation of solutions comprising a polymer and a soluble phosphate salt are given as non-limiting guides.

EXAMPLE 40

Solution Comprising Polymer 1 and Sodium Phosphate at pH 6.5

Solution 11: A solution comprising polymer 1 at 40 mg/mL and 0.45 M phosphate is prepared by mixing 8.6 mL of the solution of polymer 1 at 175.9 mg/mL described in Example 15, 17 mL of the 1 M solution of sodium phosphate described in Example 27 and 11.9 mL of water. This solution is incubated for 30 minutes at room temperature and filtered aseptically through a 0.22 μm membrane.

EXAMPLE 41

Solution Comprising Polymer 1 and Sodium Phosphate

Solution 12: A solution comprising polymer 1 at 40 mg/mL and sodium phosphate at 0.23 M is prepared by mixing 5.5 mL of the solution of polymer 1 at 175.9 mg/g described in Example 15, 5.5 mL of the 1 M solution of sodium phosphate described in Example 27 and 13.0 mL of sterile water. This solution is incubated for 30 minutes at room temperature and filtered aseptically through a 0.22 μm membrane.

EXAMPLE 42

Solution Comprising Polymer 2 and Sodium Phosphate at pH 6.5

Solution 13: A solution comprising polymer 2 at 20 mg/mL and 0.45 M phosphate is prepared by mixing 10 mL of the solution of polymer 2 at 40 mg/g described in Example 20, 9 mL of the 1 M solution of sodium phosphate described in Example 27 and 1 mL of water. This solution is incubated for 30 minutes at room temperature and filtered aseptically through a 0.22 μm membrane.

EXAMPLE 43

Solution Comprising Polymer 1, Sodium Phosphate and Hydrogen Carbonate

Solution 14: A solution comprising polymer 1 at 40 mg/mL, 0.23 M sodium phosphate and 0.31 M sodium hydrogen carbonate is prepared by mixing 5.5 mL of the solution of polymer 1 at 175.9 mg/g described in Example 15, 5.5 mL of the 1 M solution of sodium phosphate described in Example 27, 12.4 mL of a 0.6 M sodium hydrogen carbonate solution obtained by diluting the stock solution described in Example 38 and 0.6 mL of sterile water. This solution is incubated for 30 minutes at room temperature and filtered aseptically through a 0.22 μm membrane.

EXAMPLE 44

Solution Comprising Polymer 1, Sodium Phosphate and Histidine

Solution 15: A solution comprising polymer 1 at 40 mg/mL, 0.23 M sodium phosphate and 0.09 M histidine is prepared by mixing 5.5 mL of the solution of polymer 1 at 175.9 mg/g described in Example 15, 5.5 mL of the 1 M solution of sodium phosphate described in Example 27, 10.8 mL of a 0.2 M histidine solution obtained by diluting the stock solution described in Example 32 and 2.2 mL of sterile water. This solution is incubated for 30 minutes at room temperature and filtered aseptically through a 0.22 μm membrane.

EXAMPLE 45

Solution Comprising Polymer 2, Sodium Phosphate and Sodium Hydrogen Carbonate Solution 16: A solution comprising polymer 2 at 10 mg/mL, sodium phosphate at 0.23 M and sodium hydrogen carbonate at 0.31 M is prepared by mixing 3.45 mL of the solution of polymer 2 at 30.45 mg/mL described in Example 13, 2.0 mL of the 1.2 M solution of sodium phosphate obtained in Example 27, 2.7 mL of a 1.2 M sodium hydrogen carbonate solution described in Example 38 and 2.4 mL of sterile water. This solution is incubated for 30 minutes at room temperature and filtered aseptically through a 0.22 μm membrane.

EXAMPLE 46

Solution Comprising Polymer 5, Sodium Phosphate and Sodium Hydrogen Carbonate Solution 17: A solution comprising polymer 5 at 20 mg/mL, sodium phosphate at 0.23 M and sodium hydrogen carbonate at 0.31 M is prepared by mixing 1.3 mL of the solution of polymer 5 at 36.87 mg/mL described in Example 16, 0.45 mL of the 1.2 M solution of sodium phosphate obtained in Example 27 and 0.6 mL of a 1.2 M sodium hydrogen carbonate solution described in Example 38. This solution is incubated for 30 minutes at room temperature and filtered aseptically through a 0.22 μm membrane.

EXAMPLE 47

Solution Comprising Polymer 6, Sodium Phosphate and Sodium Hydrogen Carbonate Solution 18: A solution comprising polymer 6 at 20 mg/mL, sodium phosphate at 0.23 M and sodium hydrogen carbonate at 0.31 M is prepared by mixing 1.0 mL of the solution of polymer 6 at 46.7 mg/mL described in Example 17, 0.45 mL of the 1.2 M solution of sodium phosphate obtained in Example 27, 0.6 mL of a 1.2 M sodium hydrogen carbonate solution described in Example 38 and 0.3 mL of sterile water. This solution is incubated for 30 minutes at room temperature and filtered aseptically through a 0.22 μm membrane.

EXAMPLE 48

Solution Comprising Polymer 7, Sodium Phosphate and Sodium Hydrogen Carbonate Solution 19: A solution comprising polymer 7 at 40 mg/mL, sodium phosphate at 0.23 M and sodium hydrogen carbonate at 0.31 M is prepared by mixing 1.26 mL of the solution of polymer 7 at 75.9 mg/mL described in Example 18, 0.45 mL of the 1.2 M solution of sodium phosphate obtained in Example 27, 0.6 mL of a 1.2 M sodium hydrogen carbonate solution described in Example 38 and 0.06 mL of sterile water. This solution is incubated for 30 minutes at room temperature and filtered aseptically through a 0.22 μm membrane.

Examples of preparation of complexes between osteogenic proteins and polymers are given as non-limiting guides.

EXAMPLE 49

Preparation of an rhBMP-2/Polymer 1 Complex

Solution 20: 22 µl of a solution of rhBMP-2 at 1.46 mg/ml are added to 267 µl of a solution of polymer 1 at 60.0 mg/ml and 351 µL of sterile water. This solution of rhBMP-2 and of polymer 1 is at pH 7.4. This solution is incubated for two hours at 4° C. and filtered aseptically through a 0.22 µm membrane.

EXAMPLE 50

Preparation of an rhBMP-7/Polymer 1 Complex

Solution 21: 50 µl of a solution of rhBMP-7 at 1.5 mg/ml is mixed with 100 µl of a solution of polymer 1 at 60.6 mg/ml. This solution of rhBMP-7 and of polymer 1 is at pH 7.4. This solution is incubated for two hours at 4° C. and filtered aseptically through a 0.22 µm membrane.

EXAMPLE 51

Preparation of an rhBMP-7/Polymer 2 Complex

Solution 22: 50 µl of a solution of rhBMP-7 at 0.15 mg/ml is mixed with 100 µl of a solution of polymer 2 at 22.7 mg/ml. This solution of rhBMP-7 and of polymer 2 is at pH 7.4. This solution is incubated for two hours at 4° C. and filtered aseptically through a 0.22 µm membrane.

EXAMPLE 52

Preparation of an rhGDF-5/Polymer 2 Complex

Solution 23: 50 µl of a solution of rhGDF-2 at 1.5 mg/ml is mixed with 100 µl of a solution of polymer 2 at 22.7 mg/ml. This solution of rhGDF-5 and of polymer 2 is at pH 7.4. This solution is incubated for two hours at 4° C. and filtered aseptically through a 0.22 µm membrane.

EXAMPLE 53

Preparation of an rhBMP-2/Polymer 1 Complex in the Presence of Sodium Phosphate

Solution 24: 184.0 mg of rhBMP-2 lyophilizate in InFUSE buffer containing only 7.85 mg of rhBMP-2 are taken up in 19 mL of the solution described in Example 41. The solution is incubated for two hours at 4° C. The solution obtained is clear, and is filtered aseptically through a 0.22 µm membrane.

EXAMPLE 54

Preparation of an rhBMP-2/Polymer 1 Complex in the Presence of Sodium Phosphate and Sodium Hydrogen Carbonate Solution 25: 165.5 mg of rhBMP-2 lyophilizate in InFUSE buffer containing only 6.95 mg of rhBMP-2 are taken up in 17.1 mL in the solution described in Example 43. This solution is incubated for two hours at 4° C. The solution obtained is clear, and is filtered aseptically through a 0.22 µm membrane.

EXAMPLE 55

Preparation of an rhBMP-2/Polymer 1 Complex in the Presence of Sodium Phosphate and Histidine Solution 26: 165.5 mg of rhBMP-2 lyophilizate in InFUSE buffer containing only 6.95 mg of rhBMP-2 are taken up in 17.1 mL of the solution described in Example 44. The solution is incubated for two hours at 4° C. The solution obtained is clear, and is filtered aseptically through a 0.22 µm membrane.

EXAMPLE 56

Preparation of an rhBMP-2/Polymer 1 Complex in the Presence of Sodium Phosphate and Sodium Hydrogen Carbonate Solution 27: 1.98 mL of a solution of rhBMP-2 at 1.55 mg/mL in InFUSE buffer are added to 3.5 mL of the solution of polymer 1 at 174.7 mg/g. Next, 9.6 mL of a solution containing 0.74 M of sodium phosphate and 1.2 M of sodium hydrogen carbonate and 0.28 mL of sterile water are also added. This solution is incubated for 30 minutes at room temperature, and filtered aseptically through a 0.22 µm membrane. The composition of the mixture is 0.2 mg/mL of rhBMP-2, 40 mg/mL of polymer 1, 0.45 M of sodium phosphate and 0.75 M of sodium hydrogen carbonate.

EXAMPLE 57

Preparation of an rhBMP-7/Polymer 1 Complex in the Presence of Sodium Phosphate and Sodium Hydrogen Carbonate Solution 28: 1.71 mL of a solution of rhBMP-7 at 3.69 mg/mL in a 10 mM HCl buffer are added to 3.4 mL of the solution of polymer 1 at 175.9 mg/g described in Example 15. Next, 3.3 mL of the 1 M solution of sodium phosphate described in Example 27 and 7.5 mL of a solution of sodium hydrogen carbonate at 0.6 M obtained by diluting the stock solution described in Example 38, and 14.1 mL of sterile water are added. This solution is incubated for 30 minutes at room temperature, and filtered aseptically through a 0.22 µm membrane. The composition of the mixture is 0.2 mg/mL of rhBMP-7, 20 mg/mL of polymer 1, 0.11 M of sodium phosphate and 0.15 M of sodium hydrogen carbonate.

EXAMPLE 58

Preparation of an rhBMP-2/Polymer 2 Complex in the Presence of Sodium Phosphate and Sodium Hydrogen Carbonate Solution 29: 65.2 mg of a lyophilizate of rhBMP-2 in InFuse buffer are taken up in 10.5 mL of Solution 16. This solution is incubated for 1 hour at room temperature and is filtered aseptically through a 0.22 µm membrane. The composition of the mixture is 0.4 mg/mL of rhBMP-2, 10 mg/mL of polymer 2, 0.23 M of sodium phosphate and 0.31 M of sodium hydrogen carbonate.

EXAMPLE 59

Preparation of an rhBMP-2/Polymer 5 Complex in the Presence of Sodium Phosphate and Sodium Hydrogen Carbonate Solution 30: 25.7 mg of a lyophilizate of rhBMP-2 in InFuse buffer are taken up in 2.4 mL of Solution 17. This solution is incubated for 1 hour at room temperature and is filtered aseptically through a 0.22 μm membrane. The composition of the mixture is 1.5 mg/mL of rhBMP-2, 20 mg/mL of polymer 5, 0.23 M of sodium phosphate and 0.31 M of sodium hydrogen carbonate.

EXAMPLE 60

Preparation of an rhBMP-2/Polymer 6 Complex in the Presence of Sodium Phosphate and Sodium Hydrogen Carbonate Solution 31: 24.8 mg of a lyophilizate of rhBMP-2 in InFuse buffer are taken up in 2.4 mL of Solution 18. This solution is incubated for 1 hour at room temperature and is filtered aseptically through a 0.22 μm membrane. The composition of the mixture is 1.5 mg/mL of rhBMP-2, 20 mg/mL of polymer 6, 0.23 M of sodium phosphate and 0.31 M of sodium hydrogen carbonate.

EXAMPLE 61

Preparation of an rhBMP-2/Polymer 7 Complex in the Presence of Sodium Phosphate and Sodium Hydrogen Carbonate Solution 32: 25.6 mg of a lyophilizate of rhBMP-2 in InFuse buffer are taken up in 2.4 mL of Solution 19. This solution is incubated for 1 hour at room temperature and is filtered aseptically through a 0.22 μm membrane. The composition of the mixture is 1.5 mg/mL of rhBMP-2, 40 mg/mL of polymer 7, 0.23 M of sodium phosphate and 0.31 M of sodium hydrogen carbonate.

Examples of preparation of solutions comprising a soluble calcium salt and a base are given as non-limiting guides.

EXAMPLE 62

Solution of Calcium Chloride and Histidine

Solution 33: A solution containing 0.75 M calcium chloride and 0.4 M histidine is prepared by adding 112.5 mL of a 2 M calcium chloride solution, 120 mL of a 1 M histidine solution and 67.5 mL of deionized water. This solution is incubated for 30 minutes at room temperature and filtered aseptically on a 0.22 μm membrane.

EXAMPLE 63

Solution of Calcium Chloride and Proline

Solution 34: A solution containing 0.75 M calcium chloride and 0.75 M proline is prepared by adding 112.5 mL of a 2 M calcium chloride solution, 112.5 mL of a 2 M proline solution and 75 mL of deionized water. This solution is incubated for 30 minutes at room temperature and filtered aseptically on a 0.22 μm membrane.

EXAMPLE 64

Solution of Calcium Chloride and Glycine

Solution 35: A solution containing 0.75 M calcium chloride and 0.75 M glycine is prepared by adding 112.5 mL of a 2 M calcium chloride solution, 112.5 mL of a 2 M glycine solution and 75 mL of deionized water. This solution is incubated for 30 minutes at room temperature and filtered aseptically on a 0.22 μm membrane.

EXAMPLE 65

Solution of Calcium Chloride and Alanine

Solution 36: A solution containing 0.75 M calcium chloride and 0.75 M alanine is prepared by adding 112.5 mL of a 2 M calcium chloride solution, 112.5 mL of a 2 M alanine solution and 75 mL of deionized water. This solution is incubated for 30 minutes at room temperature and filtered aseptically on a 0.22 μm membrane.

EXAMPLE 66

Solution of Calcium Chloride and Lysine

Solution 37: A solution containing 0.75 M calcium chloride and 0.75 M lysine is prepared by adding 112.5 mL of 2 M calcium chloride solution, 112.5 mL of a 2 M lysine solution and 75 mL of deionized water. This solution is incubated for 30 minutes at room temperature and filtered aseptically on a 0.22 μm membrane.

EXAMPLE 67

Solution of Calcium Chloride and Serine

Solution 38: A solution containing 0.75 M calcium chloride and 0.75 M serine is prepared by adding 112.5 mL of a 2 M calcium chloride solution, 112.5 mL of a 2 M serine solution and 75 mL of deionized water. This solution is incubated for 30 minutes at room temperature and filtered aseptically on a 0.22 μm membrane.

Examples of preparation of injectable suspensions comprising a BMP, a polymer, a soluble calcium salt, a soluble phosphate salt and/or a base are given as non-limiting guides.

EXAMPLE 68

Preparation of an Injectable Suspension of an rhBMP-2/Polymer 2 Complex in the Presence of Calcium Chloride, Sodium Phosphate and Sodium Hydrogen Carbonate An osteogenic suspension based on a coprecipitation of the rhBMP-2/polymer 2 complex and of calcium phosphate particles was obtained by mixing 400 μL of Solution 29 containing rhBMP-2 at 0.4 mg/mL, i.e. 160 μg of rhBMP-2, polymer 2 at 10 mg/mL, i.e. 4 mg of polymer 2, sodium phosphate at 0.23 M, i.e. 92 μmol, and 0.31 M sodium hydrogen carbonate, i.e. 124 μmol, and 400 μL of a 0.38 M calcium chloride solution, i.e. 153 μmol. The suspension obtained is stored for 15 minutes at room temperature before injection. This suspension is injectable with 27-gauge needles.

EXAMPLE 69

Preparation of an Injectable Suspension of an rhBMP-2/Polymer 1 Complex in the Presence of Calcium Chloride, Sodium Phosphate and Sodium Hydrogen Carbonate An osteogenic suspension based on a coprecipitation of the BMP-2/polymer 1 complex and of calcium phosphate particles was obtained by mixing 1250 μL of a solution containing BMP-2 at 0.52 mg/mL, i.e. 650 μg of BMP-2, polymer 1 at 20 mg/mL, i.e. 25 mg of polymer 1, 0.23 M sodium phosphate, i.e. 288 μmol, and 0.31 M sodium hydrogen carbonate, i.e. 388 μmol, and 1250 μL of a 0.38 M calcium chloride solution, i.e. 477 μmol. The suspension obtained is stored for 15 minutes at room temperature before injection. This suspension is injectable with 27-gauge needles.

Examples of preparation of implants comprising a BMP, a polymer, a soluble calcium salt, a soluble phosphate salt and a base are given as non-limiting guides.

The implants described in the following examples are prepared with a collagen sponge of sterile crosslinked type I such as Helistat (Integra LifeSciences, Plainsboro, N.J.). The volume of this sponge varies according to the application, 200 μL for an application to an ectopic site in rats, 4.5 mL for a vertebral fusion application in rabbits.

EXAMPLE 70

Preparation of Collagen Sponge/rhBMP-2/Polymer 1 Complex Implants in the Presence of Lyophilized Calcium Chloride and Sodium Phosphate Implant 1: 40 μl of Solution 20 are introduced into a sterile 200 mm3 crosslinked collagen sponge. The solution is incubated for 30 minutes in the collagen sponge, followed by adding 10 μl of a calcium chloride solution at a concentration of 1.64 M. Finally, 90 μL of a sodium phosphate solution neutralized at a concentration of 0.053 M obtained by mixing 80 μL of sodium phosphate (22.5 mg/mL) and 10 μL of 1 N hydrochloric acid are added to the sponge. The sponge is then frozen and lyophilized aseptically. The dose of rhBMP-2 in the sponge is 2 μg.

EXAMPLE 71

Preparation of Collagen Sponge/rhBMP-2/Polymer 1 Complex Implants in the Presence of Lyophilized Calcium Chloride and Sodium Phosphate Implant 2: 40 μl of Solution 20 are introduced into a sterile 200 mm3 crosslinked collagen sponge. The solution is incubated for 30 minutes in the collagen sponge, followed by addition of 10 μl of a calcium chloride solution at a concentration of 6.85 M. Finally, 90 μL of a neutralized sodium phosphate solution at a concentration of 0.22 M obtained by mixing 80 μL of sodium phosphate (93.8 mg/mL) and 10 μL of 1 N hydrochloric acid are added to the sponge. The sponge is then frozen and lyophilized aseptically. The dose of rhBMP-2 is 2 μg.

EXAMPLE 72

Preparation of Collagen Sponge/BMP-2/Polymer 1 Complex Implants in the Presence of Lyophilized Calcium Chloride and Sodium Ascorbate Implant 3: 40 μl of Solution 20 are introduced into a sterile 200 mm3 crosslinked collagen sponge. The solution is incubated for 30 minutes in the collagen sponge, followed by addition of 10 μl of a solution of calcium chloride at a concentration of 1.64 mg/ml. Finally, 80 μL of a sodium ascorbate solution at a concentration of 0.41 M are added to the sponge. The sponge is then frozen and lyophilized aseptically. The dose of rhBMP-2 is 2 μg.

EXAMPLE 73

Preparation of Collagen Sponge/rhBMP-2/Polymer 1 Complex Implants in the Presence of Lyophilized Calcium Chloride and Sodium Phosphate Implant 4: Osteogenic implants based on a coprecipitation of the rhBMP-2/polymer 1 complex and of calcium phosphate particles were obtained from a crosslinked collagen sponge of dimensions 5.02×2.54×0.35 cm, i.e. a sponge volume of 4.52 mL. To this sponge are added 2 mL of a 0.325 mg/mL solution of rhBMP-2, i.e. 650 μg of rhBMP-2, at 64.5 mg/mL of polymer 1, i.e. 129 mg of polymer 1, and at 0.18 M of sodium phosphate at pH 7.4, i.e. 360 μmol, followed by 500 μL of a 1.2 M calcium chloride solution, i.e. 600 μmol of calcium chloride, and finally 500 μL of a 0.54 M sodium hydroxide solution, i.e. 270 μmol of sodium hydroxide. These implants are then frozen at −80° C. and lyophilized. Each of the lyophilized sponges is soaked with 1 mL of autologous blood for 30 minutes before implanting.

EXAMPLE 74

Preparation of Collagen Sponge/rhBMP-2/Polymer 1 Complex Implants in the Presence of Lyophilized Calcium Chloride and Sodium Phosphate Implant 5: Osteogenic implants based on a coprecipitation of the rhBMP-2/polymer 1 complex and of calcium phosphate particles were obtained from a crosslinked collagen sponge of dimensions 5.02×2.54×0.35 cm, i.e. a sponge volume of 4.52 mL. To this sponge are added 2 mL of a solution at 0.163 mg/mL of rhBMP-2, i.e. 326 μg of rhBMP-2, at 32.5 mg/mL of polymer 1, i.e. 65 mg of polymer 1, and at 0.18 M of sodium phosphate at pH 7.4, i.e. 360 μmol, followed by 500 μL of a 1.2 M calcium chloride solution, i.e. 600 μmol, and finally 500 μL of a 0.54 M sodium hydroxide solution, i.e. 270 μmol of sodium hydroxide. These implants are then frozen at −80° C. and lyophilized. Each of the lyophilized sponges is soaked with 1 mL of autologous blood for 30 minutes before implanting.

EXAMPLE 75

Preparation of Collagen Sponge/rhBMP-2/Polymer 1 Complex Implants in the Presence of Lyophilized Calcium Chloride and Sodium Phosphate Implant 6: Osteogenic implants based on a coprecipitation of the rhBMP-2/polymer 1 complex and of calcium phosphate particles were obtained from a crosslinked collagen sponge of dimensions 5.02×2.54×0.35 cm, i.e. a sponge volume of 4.52 mL. To this sponge are added 2 mL of a solution at 0.081 mg/mL of rhBMP-2, i.e. 162 μg of rhBMP-2, at 16.3 mg/mL of polymer 1, i.e. 32.5 mg, and at 0.18 M of sodium phosphate at pH 7.4, i.e. 360 μmol, followed by 500 μL of a 1.2 M calcium chloride solution, i.e. 600 μmol, and finally 500 μL of a 0.54 M sodium hydroxide solution, i.e. 270 μmol of sodium hydroxide. These implants are then frozen at −80° C. and lyophilized. Each of the lyophilized sponges is soaked with 1 mL of autologous blood for 30 minutes before implanting.

EXAMPLE 76

Preparation of Collagen Sponge/rhBMP-2/Polymer 4 Complex Implants in the Presence of Lyophilized Calcium Chloride and Sodium Phosphate Implant 7: Osteogenic implants based on a coprecipitation of the rhBMP-2/polymer 4 complex and of calcium phosphate particles were obtained from a crosslinked collagen sponge of dimensions 5.02×2.54×0.35 cm, i.e. a sponge volume of 4.52 mL. To this sponge are added 2 mL of a solution at 0.040 mg/mL of rhBMP-2, i.e. 80 µg of rhBMP-2, at 8 mg/mL of polymer 4, i.e. 16 mg, and at 0.18 M of sodium phosphate at pH 7.4, i.e. 360 µmol, followed by 500 µL of a 1.2 M calcium chloride solution, i.e. 600 µmol, and finally 500 µL of a 0.54 M sodium hydroxide solution, i.e. 270 µmol of sodium hydroxide. These implants are then frozen at −80° C. and lyophilized. Each of the lyophilized sponges is soaked with 1 mL of autologous blood for 30 minutes before implanting.

EXAMPLE 77

Preparation of Collagen Sponge/rhBMP-2/Polymer 4 Complex Implants in the Presence of Calcium Chloride and Sodium Phosphate Implant 8: Osteogenic implants based on a coprecipitation of the rhBMP-2/polymer 4 complex and of calcium phosphate particles were obtained from a crosslinked collagen sponge of dimensions 5.02×2.54×0.35 cm, i.e. a sponge volume of 4.52 mL. To this sponge are added 1060 µL of a solution at 0.311 mg/mL of rhBMP-2, i.e. 330 µg of rhBMP-2, at 62.3 mg/mL of polymer 4, i.e. 66 mg, and at 0.34 M of sodium phosphate at pH 7.4, i.e. 360 µmol, followed by 270 µL of a 3.4 M calcium chloride solution, i.e. 920 µmol, and finally 270 µL of a 1.37 M sodium hydroxide solution, i.e. 370 µmol of sodium hydroxide.

EXAMPLE 78

Preparation of Collagen Sponge/rhBMP-2/Polymer 4 Complex Implants in the Presence of Calcium Chloride and Sodium Phosphate Implant 9: Osteogenic implants based on a coprecipitation of the rhBMP-2/polymer 4 complex and of calcium phosphate particles were obtained from a crosslinked collagen sponge of dimensions 5.02×2.54×0.35 cm, i.e. a sponge volume of 4.52 mL. To this sponge are added 1060 µL of a solution at 0.151 mg/mL of rhBMP-2, i.e. 160 µg of rhBMP-2, at 30.2 mg/mL of polymer 4, i.e. 32 mg, and at 0.34 M of sodium phosphate at pH 7.4, i.e. 360 µmol, followed by 270 µL of a 3.4 M calcium chloride solution, i.e. 920 µmol, and finally 270 µL of a 1.37 M sodium hydroxide solution, i.e. 370 µmol of sodium hydroxide.

EXAMPLE 79

Preparation of Collagen Sponge/rhBMP-2/Polymer 4 Complex Implants in the Presence of Calcium Chloride and Sodium Phosphate Implant 10: Osteogenic implants based on a coprecipitation of the rhBMP-2/polymer 4 complex and of calcium phosphate particles were obtained from a crosslinked collagen sponge of dimensions 5.02×2.54×0.35 cm, i.e. a sponge volume of 4.52 mL. To this sponge are added 1060 µL of a solution at 0.311 mg/mL of rhBMP-2, i.e. 330 µg of rhBMP-2, at 62.3 mg/mL of polymer 4, i.e. 66 mg, and at 0.34 M of sodium phosphate at pH 7.4, i.e. 360 µmol, and finally 540 µL of a 1.7 M calcium chloride solution, i.e. 920 µmol.

EXAMPLE 80

Preparation of Collagen Sponge/rhBMP-2/Polymer 1 Complex Implants in the Presence of Lyophilized Calcium Chloride and Sodium Phosphate Implant 11: An osteogenic implant based on a precipitation of the rhBMP-2/polymer 1 complex and of calcium phosphate particles was obtained from a crosslinked collagen sponge of dimensions 5.02×2.54×0.35 cm, i.e. a sponge volume of 4.52 mL. To this sponge are added 1500 µL of a solution at 0.107 mg/mL of rhBMP-2, i.e. 160 µg of rhBMP-2, at 21.3 mg/mL of polymer 1, i.e. 32 mg, followed by 500 µL of a 1.2 M solution of calcium chloride, i.e. 600 µmol, followed by 500 µL of a 0.72 M sodium phosphate solution at pH 7.4, i.e. 360 µmol and finally 500 µL of a 0.54 M sodium hydroxide solution, i.e. 270 µmol of sodium hydroxide. The implant is then frozen at −80° C. and lyophilized. The lyophilized sponge is soaked with 1 mL of autologous blood for 30 minutes before implanting.

EXAMPLE 81

Preparation of Collagen Sponge/rhBMP-2/Polymer 4 Complex Implants in the Presence of Calcium Chloride, Sodium Phosphate and Histidine Implant 12: Osteogenic implants based on a coprecipitation of the rhBMP-2/polymer 4 complex and of calcium phosphate particles were obtained from a crosslinked collagen sponge of dimensions 5.02×2.54×0.35 cm, i.e. a sponge volume of 4.52 mL. To this sponge are added 800 µL of a solution at 0.413 mg/mL of rhBMP-2, i.e. 330 µg of rhBMP-2, at 20.65 mg/mL of polymer 4, i.e. 16.5 mg, and at 0.115 M of sodium phosphate at pH 7.4, i.e. 92 µmol, and finally 800 µL of a 0.3 M calcium chloride solution, i.e. 240 µmol, and at 0.2 M of histidine, i.e. 160 µmol.

EXAMPLE 82

Preparation of Collagen Sponge/rhBMP-2/Polymer 4 Complex Implants in the Presence of Calcium Chloride, Sodium Phosphate and Histidine Implant 13: Osteogenic implants based on a coprecipitation of the rhBMP-2/polymer 4 complex and of calcium phosphate particles were obtained from a crosslinked collagen sponge of dimensions 5.02×2.54×0.35 cm, i.e. a sponge volume of 4.52 mL. To this sponge are added 800 µL of a solution at 0.413 mg/mL of rhBMP-2, i.e. 330 µg of rhBMP-2, at 20.65 mg/mL of polymer 4, i.e. 16.5 mg, and at 0.24 M of sodium phosphate at pH 7.4, i.e. 192 µmol, and finally 800 µL of a 0.4 M calcium chloride solution, i.e. 320 µmol and at 0.4 M of histidine, i.e. 320 µmol.

EXAMPLE 83

Preparation of Collagen Sponge/rhBMP-2/Polymer 1 Complex Implants in the Presence of Calcium Chloride, Sodium Phosphate and Sodium Hydrogen Carbonate Implant 14: Osteogenic implants based on a coprecipitation of the rhBMP-2/polymer 1 complex and of calcium phosphate particles were obtained from a crosslinked collagen sponge of dimensions 5.02×2.54×0.35 cm, i.e. a sponge volume of 4.52 mL. To this sponge are added 800 µL of a solution at 0.2 mg/mL of rhBMP-2, i.e. 160 μg of rhBMP-2, at 40 mg/mL of polymer 1, i.e. 32 mg, at 0.45 M of sodium phosphate at pH 7.4, i.e. 360 μmol, and at 0.75 M of sodium hydrogen carbonate, i.e. 600 μmol, and finally 800 μL of a 0.75 M calcium chloride solution, i.e. 600 μmol.

EXAMPLE 84

Preparation of Collagen Sponge/rhBMP-2/Polymer 1 Complex Implants in the Presence of Calcium Chloride, Sodium Phosphate and Sodium Hydrogen Carbonate Implant 15: Osteogenic implants based on a coprecipitation of the rhBMP-2/polymer 1 complex and of calcium phosphate particles were obtained from a crosslinked collagen sponge of dimensions 5.02×2.54×0.35 cm, i.e. a sponge volume of 4.52 mL. To this sponge are added 800 μL of a solution containing BMP-2 at 0.2 mg/mL, i.e. 160 μg of rhBMP-2, polymer 1 at 8 mg/mL, i.e. 6.4 mg, sodium phosphate at 0.45 M, i.e. 360 μmol, and sodium hydrogen carbonate at 0.75 M, i.e. 600 μmol, and finally 800 μL of a calcium chloride solution at 0.75 M, i.e. 600 μmol.

EXAMPLE 85

Preparation of Collagen Sponge/rhBMP-2/Polymer 1 Complex Implants in the Presence of Calcium Chloride, Sodium Phosphate and Sodium Hydrogen Carbonate Implant 16: Osteogenic implants based on a coprecipitation of the rhBMP-2/polymer 1 complex and of calcium phosphate particles were obtained from a crosslinked collagen sponge of dimensions 5.02×2.54×0.35 cm, i.e. a sponge volume of 4.52 mL. To this sponge are added 800 μL of a solution containing BMP-2 at 0.2 mg/mL, i.e. 160 μg of rhBMP-2, polymer 1 at 20.6 mg/mL, i.e. 16.5 mg, sodium phosphate at 0.24 M, i.e. 192 μmol, and sodium hydrogen carbonate at 0.75 M, i.e. 600 μmol, and finally 800 μL of a calcium chloride solution at 0.4 M, i.e. 320 μmol.

EXAMPLE 86

Preparation of Collagen Sponge/rhBMP-7/Polymer 1 Complex Implants in the Presence of Calcium Chloride, Sodium Phosphate and Sodium Hydrogen Carbonate Implant 17: Osteogenic implants based on a coprecipitation of the BMP-7/polymer 1 complex and of calcium phosphate particles were obtained after successive impregnations of a cylindrical crosslinked type I collagen sponge of 198 μL with 70 μL of a solution at 0.071 mg/mL of BMP-7, i.e. 5 μg of BMP-7, at 31.3 mg/mL of polymer 1, i.e. 1.5 mg of polymer 1, at 0.24 M of sodium phosphate at pH 7.4, i.e. 16.8 μmol, and at 0.4 M of sodium hydrogen carbonate, i.e. 28 μmol, then with 70 μl of a solution at 0.4 M of calcium chloride, i.e. 28 μmol. The implants are then frozen at −80° C. and lyophilized. The lyophilized sponges are soaked with 45 μL of autologous blood for 30 minutes before implanting.

EXAMPLE 87

Preparation of Collagen Sponge/rhBMP-2/Polymer 2 Complex Implants in the Presence of Calcium Chloride, Sodium Phosphate and Sodium Hydrogen Carbonate Implant 18: Osteogenic implants based on a coprecipitation of the rhBMP-2/polymer 2 complex and of calcium phosphate particles were obtained from a crosslinked collagen sponge with a sponge volume of 2.25 mL. 400 μL of solution 29 containing rhBMP-2 at 0.4 mg/mL, i.e. 160 μg of rhBMP-2, polymer 2 at 10 mg/mL, i.e. 4 mg, sodium phosphate at 0.23 M, i.e. 92 μmol and sodium hydrogen carbonate at 0.31 M, i.e. 124 μmol, and finally 400 μL of a 0.38 M calcium chloride solution, i.e. 153 μmol, are added to this sponge. Each solution is left for 15 minutes in contact with the sponge after addition. After these impregnation times, the sponge is ready for implantation.

EXAMPLE 88

Preparation of Collagen Sponge/rhBMP-7/Polymer 3 Complex Implants in the Presence of Calcium Chloride, Sodium Phosphate and Sodium Hydrogen Carbonate Implant 19: Osteogenic implants based on a coprecipitation of the BMP-7/polymer 3 complex and of calcium phosphate particles were obtained after successive impregnations of a crosslinked type I collagen sponge 4520 μL in volume with 800 μL of a solution containing BMP-7 at 0.41 mg/mL, i.e. 330 μg of BMP-7, polymer 3 at 17.5 mg/mL, i.e. 14 mg of polymer 3, 0.45 M sodium phosphate, i.e. 360 μmol, and then 800 μL of a solution containing calcium chloride at 0.4 M, i.e. 648 μmol, and of proline at 0.61 M, i.e. 488 μmol. Each solution is left for 15 minutes in contact with the sponge after addition. After these impregnation times, the sponge is ready for implanting.

EXAMPLE 89

Preparation of Collagen Sponge/rhGDF-5/Polymer 2 Complex Implants in the Presence of Lyophilized Calcium Chloride, Sodium Phosphate and Histidine Implant 20: Osteogenic implants based on a coprecipitation of the GDF-5/polymer 2 complex and of calcium phosphate particles were obtained after successive impregnations of a crosslinked type I collagen sponge 4520 μL in volume with 1500 μL of a solution containing GDF-5 at 0.5 mg/mL, i.e. 750 μg of GDF-5, polymer 2 at 20 mg/mL, i.e. 30 mg of polymer 2, and then 750 μL of a solution containing calcium chloride at 0.8 M, i.e. 600 μmol and histidine at 0.38 M, i.e. 285 μmol, and finally with a solution containing sodium phosphate at 0.48 M, i.e. 360 μmol. Each solution is left for 15 minutes in contact with the sponge after addition. After these impregnation times, the sponges are frozen at −80° C. and lyophilized. The lyophilized sponges are soaked with 1.5 mL of autologous blood 30 minutes before implantation.

The implants described in the following examples are prepared with a Compressive-Resistant Matrix, CRM. This material is a mixed matrix composed of type I bovine collagen and of a calcium phosphate mineral phase composed of 15% hydroxyapatite and 85% beta-tricalcium phosphate sold by Medtronic under the name MasterGraft Matrix. The volume of this matrix varies according to the application, 140 μl for an application to an ectopic site in rats, and 5 mL for a vertebral fusion application in rabbits.

EXAMPLE 90

Preparation of Collagen Sponge Implants Surrounding a CRM Containing an rhBMP-2/Polymer 2 Complex in the Presence of Calcium Chloride, Sodium Phosphate and Sodium Hydrogen Carbonate Implant 21: Implant 16 is rolled up around a dry CRM 5.0 mL in volume (5.0*1.0*1.0 cm) before implantation into the rabbit.

EXAMPLE 91

Preparation of CRM/rhBMP-2/Polymer 2 Complex Implants in the Presence of Calcium Chloride, Sodium Phosphate and Sodium Hydrogen Carbonate Implant 22: Osteogenic implants based on a coprecipitation of the BMP-2/polymer 2 complex and of calcium phosphate particles were obtained after successive impregnations of a CRM 140 µL in volume with 35 µL of a solution at 0.14 mg/mL of BMP-2, i.e. 5 µg of BMP-2, at 14 mg/mL of polymer 2, i.e. 0.5 mg of polymer 2, at 0.23 M of sodium phosphate, i.e. 8 µmol, and at 0.31 M of sodium hydrogen carbonate, i.e. 11 µmol, for 15 minutes, followed by 35 µL of a solution at 0.38 M of calcium chloride, i.e. 13 µmol, for 15 minutes. The CRMs are ready for implantation.

EXAMPLE 92

Preparation of CRM/rhGDF-5/Polymer 2 Complex Implants in the Presence of Lyophilized Calcium Chloride, Sodium Phosphate and Histidine Implant 23: Osteogenic implants based on a coprecipitation of the GDF-5/polymer 2 complex and of calcium phosphate particles were obtained after successive impregnations of a CRM 140 µL in volume with 35 µL of a solution at 0.86 mg/mL of GDF-5, i.e. 30 µg of GDF-5, at 14 mg/mL of polymer 2, i.e. 0.5 mg of polymer 2, at 0.23 M of sodium phosphate, i.e. 8 µmol, for 15 minutes, and then with 17.5 µL of a histidine solution at 0.34 M, i.e. 6 µmol, for 15 minutes, and finally with 17.5 µL of a calcium chloride solution at 0.74 M, i.e. 13 µmol. The CRMs are then frozen at −80° C. and lyophilized. The lyophilized CRMs are soaked with 45 µL of autologous blood 30 minutes before implanting.

EXAMPLE 93

Preparation of CRM/rhBMP-2/Polymer 1 Complex Implants in the Presence of Calcium Chloride, Sodium Phosphate and Sodium Hydrogen Carbonate Implant 24: Osteogenic implants based on a coprecipitation of the BMP-2/polymer 1 complex and of calcium phosphate particles were obtained after successive impregnations of a CRM 5.0 mL in volume with 1250 µL of a solution at 0.52 mg/mL of BMP-2, i.e. 650 µg of BMP-2, at 20 mg/mL of polymer 1, i.e. 25 mg of polymer 1, at 0.23 M of sodium phosphate, i.e. 288 µmol, and at 0.31 M of sodium hydrogen carbonate, i.e. 388 µmol, for 15 minutes, and then with 1250 µL of a solution at 0.38 M of calcium chloride, i.e. 477 µmol, for 15 minutes. The CRMs are ready for implanting.

COUNTEREXAMPLE 1

Preparation of Collagen Sponge Implants Containing 20 µg of rhBMP-2

Implant 25: 40 µl of a 0.5 mg/ml solution of rhBMP-2 in a buffer of Infuse type are introduced aseptically into a sterile 200 mm3 crosslinked collagen sponge. The solution is left for 30 minutes in the collagen sponge before implanting.
The dose of rhBMP-2 in implant 25 is 20 µg.

COUNTEREXAMPLE 2

Preparation of Collagen Sponge Implants Containing 2 µg of rhBMP-2

Implant 26: 40 µl of a 0.05 mg/ml solution of rhBMP-2 in a buffer of Infuse type are introduced aseptically into a sterile 200 mm3 crosslinked collagen sponge of Helistat type (Integra LifeSciences, Plainsboro, N.J.). The solution is left for 30 minutes in the collagen sponge before implanting.
The dose of rhBMP-2 in implant 26 is 2 µg.

COUNTEREXAMPLE 3

Preparation of Collagen Sponge Implants Containing 5 µg of rhBMP-7

Implant 27: Lyophilized osteogenic implants based on BMP-7 were obtained after impregnating a cylindrical crosslinked type I collagen sponge of 198 µL with 140 µL of a solution at 0.036 mg/mL of BMP-7, i.e. 5 µg. The implants are then frozen at −80° C. and lyophilized. The lyophilized sponges are soaked with 45 µL of autologous blood 30 minutes before implanting.

COUNTEREXAMPLE 4

Preparation of Collagen Sponge Implants Containing 2.3 mg of rhBMP-2

Implant 28: Osteogenic implants were obtained by impregnating a crosslinked type I collagen sponge of dimensions 5.02×2.54×0.35 cm, i.e. a sponge volume of 4.52 mL, with 1600 µL of a solution at 1.45 mg/mL of rhBMP-2, i.e. 2.3 mg. The solution is left for 30 minutes in the collagen sponge before implanting.

COUNTEREXAMPLE 5

Preparation of Collagen Sponge Implants Containing 1.3 mg of rhBMP-2

Implant 29: Osteogenic implants were obtained by impregnating a crosslinked type I collagen sponge of dimensions 5.02×2.54×0.35 cm, i.e. a sponge volume of 4.52 mL, with 1600 µL of a solution at 0.80 mg/mL of rhBMP-2, i.e. 1.3 mg. The solution is left for 30 minutes in the collagen sponge before implanting.

EXAMPLE 94

Evaluation of the Osteo-Inductive Power of the Various Formulations

The object of this study is to demonstrate the osteo-inductive power of the various formulations in a model of ectopic bone formation in rats. Male rats weighing 150 to 250 g (Sprague Dawley OFA-SD, Charles River Laboratories France, B.P. 109, 69592 l'Arbresle) are used for this study.

An analgesic treatment (buprenorphine, Temgesic®, Pfizer, France) is administered before the surgical intervention. The rats are anesthetized by inhalation of a mixture of O2 and isoflurane (1-4%). The fur is removed by shaving over a wide dorsal area. The skin of this dorsal area is disinfected with a povidone iodine solution (Vetedine® solution, Vetoquinol, France).

Paravertebral incisions of about 1 cm are made so as to expose the right and left paravertebral dorsal muscles. Access to the muscles is made by transfacial incision. Each of the implants is placed in a pocket such that no compression can be exerted thereon. Four implants are implanted per rat (two implants per site). The implant opening is then sutured using polypropylene yarn (Prolene 4/0, Ethicon, France). The skin is closed up using a non-absorbable suture. The rats are then returned to their respective cages and kept under observation during their recovery.

At 21 days, the animals are anesthetized by injection of tiletamine-zolazepam (ZOLETIL®25-50 mg/kg, IM, VIRBAC, France).

The animals are then sacrificed by injection of a dose of pentobarbital (DOLETHAL®, VETOQUINOL, France). Each site is then observed macroscopically, any sign of local intolerance (inflammation, necrosis, hemorrhage) and the presence of bony and/or cartilaginous tissue is recorded and rated according to the following scale: 0: absence, 1: weak, 2: moderate, 3: marked, 4: sizable.

Each of the explants is removed from its site of implantation and macroscopic photographs are taken. The size and weight of the explants are then determined. Each explant is then stored in buffered 10% formaldehyde solution.

Results:

This in vivo experiment makes it possible to measure the osteo-inducing effect of rhBMP-2 placed in a dorsal muscle of a rat. This non-bony site is said to be ectopic. The results of the various examples are collated in the following table.

|  | Presence of bony tissue | Mass of explants (mg) |
|---|---|---|
| Implant 25 | 3.6 | 38 |
| Implant 26 | — | — |
| Implant 1 | 3.4 | 100 |
| Implant 2 | 3.1 | 132 |
| Implant 3 | 3.5 | 124 |

A dose of 20 µg of rhBMP-2 in a collagen sponge (Implant 25, Counterexample 1) leads to the obtention of ossified explants with an average mass of 38 mg after 21 days.

A dose of 2 µg of rhBMP-2 in a collagen sponge (Implant 26, Counterexample 2) does not have any osteo-inductive power that is sufficient for the collagen implants to be able to be found after 21 days.

In the presence of rhBMP-2/polymer 1 complex, calcium chloride and sodium phosphate, a dose of rhBMP-2 of 2 µg lyophilized in the collagen sponge (Implant 1, Example 70 and Implant 2, Example 71) makes it possible to generate ossified explants, in contrast with rhBMP-2 alone at the same dose. Furthermore, these explants have a mass 4 times greater with a bone score equivalent to those with rhBMP-2 alone. This formulation thus makes it possible to improve the osteogenic activity of rhBMP-2.

In an equivalent manner, the addition of sodium ascorbate to the collagen sponge containing the rhBMP-2/polymer 1 complex and calcium chloride (Implant 3, Example 72) also makes it possible to obtain ossified explants four times greater in mass with a bone score equivalent to that with rhBMP-2 alone. This formulation also makes it possible to improve the osteogenic activity of rhBMP-2.

EXAMPLE 95

Evaluation of the Osteo-Inductive Power of the Various Formulations in Postero-Lateral Fusion The object of this study is to demonstrate the osteo-inducing power of the various formulations in a model of posterolateral fusion in rabbits. This study is conducted according to the experimental protocol described in the publication by J. P. Lawrence (Lawrence, J. P. et al., Spine 2007, 32 (11), 1206-1213), with the exception of the treatment with nicotine, since the induction of a pseudarthrosis is not desired.

Fusion of the vertebrae is evaluated by manual palpation of the explanted spinal column. The absence of mobility between the vertebrae is synonymous with fusion. The spinal column is also analyzed by micro-CT at 12 weeks to evaluate the presence of bone in vertebrae. The results obtained for the various implants are summarized in the following table.

| | Protein | Dose of BMP-2 (mg) | Fusion |
|---|---|---|---|
| Implant 28 | BMP-2 | 2.3 | 2/2 |
| Implant 29 | BMP-2 | 1.3 | 7/8 |
| Implant 5 | BMP-2 | 0.33 | 3/3 |
| Implant 14 | BMP-2 | 0.16 | 5/5 |
| Implant 15 | BMP-2 | 0.16 | 6/6 |
| Implant 16 | BMP-2 | 0.16 | 6/6 |
| Implant 19 | BMP-7 | 0.33 | 2/2 |
| Implant 20 | GDF-5 | 0.75 | 5/5 |

From these posterolateral fusion studies in rabbits, it emerges that the BMP-2/polymer 2 complex coprecipitated with the calcium phosphate salt makes it possible to reduce the BMP-2 doses by a factor of 4 to 8 times with respect to BMP-2 alone at 1.3 mg of BMP-2 alone, this being an effective dose in this model according to the literature, with equivalent fusion results. Even at BMP-2 doses of 0.16 mg, posterolateral fusion is observed in all the rabbits in the case of the BMP-2/polymer complex coprecipitated with the calcium phosphate salt.

The implants containing the BMP-7/copolymer complex coprecipitated with the calcium phosphate salt also lead to vertebral fusion for low doses of BMP-7, 0.33 mg of BMP-7 per implant. The literature results demonstrate that vertebral fusion in rabbits of 100% is not achieved even at a dose of 3.5 mg of BMP-7, this dose being far superior to that studied (Yao, G. et al., Spine 2008, 33 (18), 1935-1942).

The implants containing the GDF-5/polymer complex coprecipitated with the calcium phosphate salt also lead to 100% vertebral fusion for low doses of GDF-5, 750 µg of GDF-5 per implant. The literature results demonstrate that vertebral fusion in rabbits of 100% is not achieved, even for a dose of 2.5 mg of GDF-5, this dose being far superior to that studied (Magit, David P. et al., Spine 2006, 31 (19), 2180-2188).

The invention claimed is:

1. A coprecipitate comprising at least one complex and at least one insoluble calcium salt, said coprecipitate being in a divided form, said complex being in its insolubilized form and being a complex between an osteogenic protein selected from the group consisting of bone morphogenetic proteins and growth/differentiation factors, wherein the bone morphogenetic proteins and growth/differentiation factors are selected from the group consisting of BMP-2 (dibotermine-alpha), BMP-4, BMP-7 (eptotermine-alpha), BMP-14, GDF 5, and combinations thereof, and a functionalized dextran selected from the group consisting of dextrans comprising carboxyl functional groups partly substituted with hydrophobic alcohols, of general formula IX:

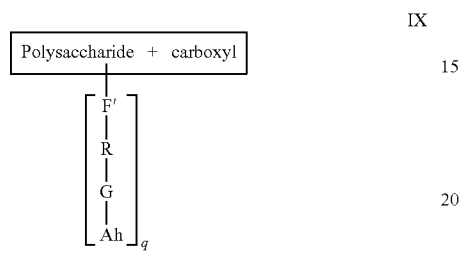

IX in which q represents the mole fraction of carboxyl functions of the dextran that are substituted with F'—R-G-Ah and is between 0.01 and 0.7, F' being an amide function, G being an ester, thioester, carbonate or carbamate function, R being a chain comprising between 1 and 18 carbons, optionally branched and/or unsaturated, optionally comprising one or more heteroatoms, and having at least one acid function, Ah being a hydrophobic alcohol residue, produced by coupling between a hydroxyl function of a hydrophobic alcohol and at least one electrophilic function borne by the group R, wherein when the carboxyl function of the dextran is not substituted with F'—R-G-Ah, then the carboxyl functional group(s) of the dextran are carboxylates of a cation, and wherein when the dextran comprises carboxyl functional groups, the dextran is amphiphilic at neutral pH.

2. The coprecipitate as claimed in claim 1, in which the insoluble calcium salt is chosen from the group consisting of calcium orthophosphates in anhydrous or hydrated form, alone or as a mixture.

3. The coprecipitate as claimed in claim 1, which also comprises at least one insoluble calcium salt chosen from the group consisting of calcium oxalate, calcium ascorbate, calcium carbonate and calcium sulfate.

4. The coprecipitate as claimed in claim 1, in which the insoluble calcium salt is chosen from the group consisting of mixed salts formed between cationic calcium ions and anionic ions selected from the group consisting of mono-, di- or tribasic phosphates, dextran carboxylates, carbonates, hydroxides and basic anions.

5. The coprecipitate as claimed in claim 1, wherein the complex further includes an additional material with chemo-attracting and angiogenic power selected from the group consisting of platelet derived growth factors and vascular endothelial growth factors.

6. The coprecipitate as claimed in claim 5, in which the at least one material with chemo-attracting and angiogenic power is platelet derived growth factor (PDGF).

7. The coprecipitate as claimed in claim 5, which comprises at least BMP-2 and PDGF-BB.

8. The coprecipitate as claimed in claim 5, which comprises at least BMP-7 and PDGF-BB.

9. The coprecipitate as claimed in claim 5, which comprises at least GDF-5 and PDGF-BB.

10. The coprecipitate as claimed in claim 5, wherein the at least one material with chemo-attracting and angiogenic power is vascular endothelial growth factor (VEGF).

11. The coprecipitate as claimed in claim 1, wherein the dextrans comprising carboxyl functional groups are synthetic dextrans obtained from dextrans on which at least 15 carboxyl functional groups per 100 saccharide units have been grafted, of general formula X:

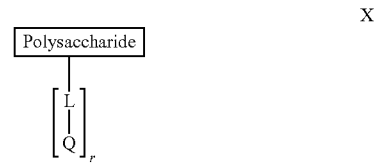

X

L being a bond resulting from coupling between linker Q and a hydroxyl function of the dextran, and being either an ester, thioester, carbonate, carbamate or ether function, r represents the mole fraction of the substituents L-Q per saccharide unit of the polysaccharide, Q being a chain comprising between 1 and 18 carbons, optionally branched and/or unsaturated, comprising one or more heteroatoms, and comprising at least one carboxyl functional group, $CO_2H$.

12. A coprecipitate comprising at least one complex and at least one insoluble calcium salt, said coprecipitate being in a divided form, said complex being in its insolubilized form and being a complex between an osteogenic protein selected from the group consisting of bone morphogenetic proteins and growth/differentiation factors, wherein the bone morphogenetic proteins and growth/differentiation factors are selected from the group consisting of BMP-2 (dibotermine-alpha), BMP-4, BMP-7 (eptotermine-alpha), BMP-14, GDF 5, and combinations thereof, and a functionalized dextran selected from the group consisting of dextrans of general formula III:

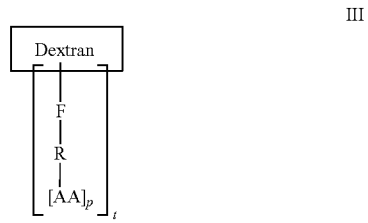

III

R being a chain comprising between 1 and 18 carbons, optionally branched and/or unsaturated, comprising one or more heteroatoms, and having at least one acid function, F resulting from the coupling between linker R and a hydroxyl function of the dextran, being either an ester, thioester, amide, carbonate, carbamate, ether, thioether or amine function, AA being a hydrophobic amino acid residue, L or D, produced by the coupling between the amine of the amino acid and an acid borne by the group R, said hydrophobic amino acid being selected from the group consisting of tryptophan, tryptophanol, tryptophanamide and 2 indolethylamine, salts thereof of an alkali metal cation, phenylalanine, leucine, isoleucine and valine, and alcohol, amide or decarboxylated derivatives thereof, t represents the mole fraction of the substituent F—R—[AA]$_p$ per glycoside unit, and is between 0.1 and 2, p represents the mole fraction of groups R substituted with AA and is between 0.05 and 1, and wherein when R is not substituted by AA, then the acid(s) of the group R are carboxylates of a cation.

13. A kit for preparing an osteogenic implant, comprising at least:
a: a composition comprising at least one osteogenic protein selected from the group consisting of bone morphogenetic proteins and growth/differentiation factors, the bone morphogenetic proteins and growth/differentiation factors are selected from the group consisting of BMP-2 (dibotermine-alpha), BMP-4, BMP-7 (eptotermine-alpha), BMP-14, GDF-5, and combinations thereof,
b: a composition comprising at least one functionalized dextran, wherein
the functionalized dextran is selected from the group consisting of dextrans comprising carboxyl functional groups partly substituted with hydrophobic alcohols, of general formula IX:

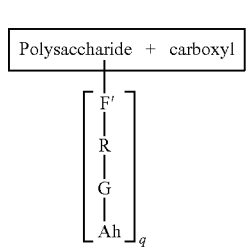

IX in which q represents the mole fraction of carboxyl functions of the dextran that are substituted with F'—R-G-Ah and is between 0.01 and 0.7,
F' being an amide function,
G being an ester, thioester, carbonate or carbamate function,
R being a chain comprising between 1 and 18 carbons, optionally branched and/or unsaturated, optionally comprising one or more heteroatoms, and having at least one acid function,
Ah being a hydrophobic alcohol residue, produced by coupling between a hydroxyl function of a hydrophobic alcohol and at least one electrophilic function borne by the group R,
wherein when the carboxyl function of the dextran is not substituted with F'—R-G-Ah, then the carboxyl functional group(s) of the dextran are carboxylates of a cation, and
wherein when the dextran comprises carboxyl functional groups, the dextran is amphiphilic at neutral pH,
c: a composition comprising at least one soluble calcium salt, and
d: a composition comprising at least one soluble salt of an anion capable of forming an insoluble calcium salt.

14. The kit as claimed in claim 13, also comprising an additional composition comprising at least one base.

15. The kit as claimed in claim 14, also comprising a second base that may be added to compositions b, c or d.

16. The kit as claimed in claim 13, in which the composition comprising the osteogenic protein may also comprise the functionalized dextran for forming the complex.

17. The kit as claimed in claim 13, in which the composition comprising the osteogenic protein may also comprise the soluble salt of an anion capable of forming an insoluble calcium salt and/or a base.

18. The kit as claimed in claim 13, in which the composition comprising the functionalized dextran may also comprise the soluble salt of an anion capable of forming an insoluble calcium salt and/or a base.

19. The kit as claimed in claim 13, in which the composition comprising the soluble calcium salt may also comprise a base.

20. The kit as claimed in claim 13, in which the soluble calcium salt is chosen from the group consisting of calcium chloride, D-gluconate, formate, D-saccharate, acetate, L-lactate, glutamate and aspartate.

21. The kit as claimed in claim 13, in which the soluble calcium salt is calcium chloride.

22. The kit as claimed in claim 13, in which the soluble salt of an anion capable of forming a precipitate with the calcium ion is a soluble salt whose anion is chosen from the group consisting of phosphate anions comprising the phosphate ion $PO_4^{3-}$, the hydrogen phosphate ion $HPO_4^{2-}$ and the dihydrogen phosphate ion $H_2PO_4^-$.

23. The kit as claimed in claim 13, in which the base is chosen from mineral and organic bases.

24. The kit as claimed in claim 23, in which the mineral base is chosen from the group consisting of sodium hydroxide, sodium hydrogen carbonate and sodium carbonate.

25. The kit as claimed in claim 23, in which the organic base is chosen from the group consisting of amines and deprotonated amino acids.

26. The kit as claimed in claim 23, in which the organic base is chosen from the group consisting of imidazole and derivatives thereof.

27. The kit as claimed in claim 13, which also comprises at least one organic matrix or a mineral matrix or a mixed matrix.

28. The kit as claimed in claim 27, in which the matrix is an organic matrix chosen from the group consisting of hydrogels and/or matrices based on a crosslinked polymer.

29. The kit as claimed in claim 28, in which the hydrogel is a hydrogel obtained by chemical or physical crosslinking of polymer chains.

30. The kit as claimed in claim 28, in which the crosslinked polymer is crosslinked and sterilized purified natural collagen.

31. The kit as claimed in claim 29, in which the hydrogel is chosen from the group of synthetic polymers including copolymers of ethylene glycol and of lactic acid, copolymers of ethylene glycol and of glycolic acid, poly(N-vinylpyrrolidone), polyvinylic acids, and polyacrylamides and polyacrylic acids.

32. The kit as claimed in claim 28, in which the hydrogel is chosen from the group consisting of natural polymers including hyaluronic acid, keratan, pullulan, pectin, dextran, cellulose and cellulose derivatives, alginic acid, xanthan, carrageenan, chitosan, chondroitin, collagen, gelatin, polylysine, fibrin, and biologically acceptable salts thereof.

33. The kit as claimed in claim 13, in which the compositions constituting the kit are aqueous solutions.

34. The kit as claimed in claim 13, in which the compositions constituting the kit are lyophilizates.

35. The kit as claimed in claim 13, wherein the composition a: further comprises an additional composition comprising at least one material with chemo-attracting and angiogenic power selected from the group consisting of platelet derived growth factors and vascular endothelial growth factors.

36. The kit as claimed in claim 34, in which the at least one material with chemo-attracting and angiogenic power is platelet derived growth factor (PDGF).

37. The kit as claimed in claim 34, which comprises at least BMP-2 and PDGF-BB.

38. The kit as claimed in claim 34, which comprises at least BMP-7 and PDGF-BB.

39. The kit as claimed in claim 34, which comprises at least GDF-5 and PDGF-BB.

40. The kit as claimed in claim 34, in which the at least one material with chemo-attracting and angiogenic power is vascular endothelial growth factor (VEGF).

41. A kit comprising:
   a: a composition comprising at least one osteogenic protein selected from the group consisting of bone morphogenetic proteins and growth/differentiation factors, the bone morphogenetic proteins and growth/differentiation factors are selected from the group consisting of BMP-2 (dibotermine-alpha), BMP-4, BMP-7 (eptotermine-alpha), BMP-14, GDF-5, and combinations thereof,
   b: a composition comprising at least one functionalized dextran, at least one base and at least one soluble salt of an anion capable of forming an insoluble calcium salt, wherein the functionalized dextran is selected from the group consisting of dextrans comprising carboxyl functional groups partly substituted with hydrophobic alcohols, of general formula IX:

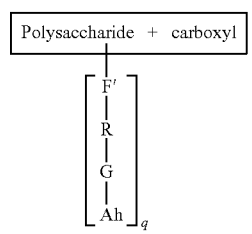

IX in which q represents the mole fraction of carboxyl functions of the dextran that are substituted with F'—R-G-Ah and is between 0.01 and 0.7,
F' being an amide function, G being an ester, thioester, carbonate or carbamate function,
R being a chain comprising between 1 and 18 carbons, optionally branched and/or unsaturated, optionally comprising one or more heteroatoms, and having at least one acid function,
Ah being a hydrophobic alcohol residue, produced by coupling between a hydroxyl function of a hydrophobic alcohol and at least one electrophilic function borne by the group R,
wherein when the carboxyl function of the dextran is not substituted with F'—R-G-Ah, then the carboxyl functional group(s) of the dextran are carboxylates of a cation,
wherein when the dextran comprises carboxyl functional groups, the dextran is amphiphilic at neutral pH, and
c: a composition comprising at least one soluble calcium salt.

42. A kit comprising:
   a: a composition comprising at least one osteogenic protein selected from the group consisting of bone morphogenetic proteins and growth/differentiation factors, the bone morphogenetic proteins and growth/differentiation factors are selected from the group consisting of BMP-2 (dibotermine-alpha), BMP-4, BMP-7 (eptotermine-alpha), BMP-14, GDF-5, and combinations thereof,
   b: a composition comprising at least one functionalized dextran and at least one soluble salt of an anion capable of forming an insoluble calcium salt, wherein the functionalized dextran is selected from the group consisting of dextrans comprising carboxyl functional groups partly substituted with hydrophobic alcohols, of general formula IX:

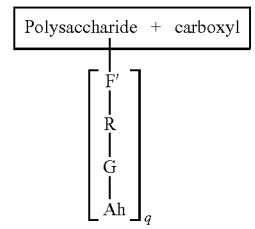

IX in which q represents the mole fraction of carboxyl functions of the dextran that are substituted with F'—R-G-Ah and is between 0.01 and 0.7,
F' being an amide function,
G being an ester, thioester, carbonate or carbamate function,
R being a chain comprising between 1 and 18 carbons, optionally branched and/or unsaturated, optionally comprising one or more heteroatoms, and having at least one acid function,
Ah being a hydrophobic alcohol residue, produced by coupling between a hydroxyl function of a hydrophobic alcohol and at least one electrophilic function borne by the group R,
wherein when the carboxyl function of the dextran is not substituted with F'—R-G-Ah, then the carboxyl functional group(s) of the dextran are carboxylates of a cation,
wherein when the dextran comprises carboxyl functional groups, the dextran is amphiphilic at neutral pH, and
c: a composition comprising at least one soluble calcium salt and at least one base.

43. The kit as claimed in claim 42, wherein the dextrans comprising carboxyl functional groups are synthetic dextrans obtained from dextran on which at least 15 carboxyl functional groups per 100 saccharide units have been grafted, of general formula X:

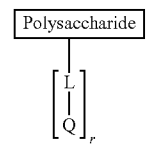

X

L being a bond resulting from coupling between linker Q and a hydroxyl function of the dextran, and being either an ester, thioester, carbonate, carbamate or ether function, r represents the mole fraction of the substituents L-Q per saccharide unit of the dextran, and Q being a chain comprising between 1 and 18 carbons, optionally branched and/or unsaturated, comprising one or more heteroatoms, and comprising at least one carboxyl functional group, $CO_2H$.

44. A kit comprising:
- a: a composition comprising at least one osteogenic protein selected from the group consisting of bone morphogenetic proteins and growth/differentiation factors, the bone morphogenetic proteins and growth/differentiation factors are selected from the group consisting of BMP-2 (dibotermine-alpha), BMP-4, BMP-7 (eptotermine-alpha), BMP-14, GDF-5, and combinations thereof,
- b: a composition comprising at least one functionalized dextran and at least one soluble salt of an anion capable of forming an insoluble calcium salt, wherein the functionalized dextran is selected from the group consisting of functionalized dextrans of general formula III below:

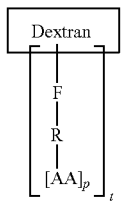

III

R being a chain comprising between 1 and 18 carbons, optionally branched and/or unsaturated, comprising one or more heteroatoms, and having at least one acid function, F resulting from the coupling between linker R and a hydroxyl function of the dextran, being either an ester, thioester, amide, carbonate, carbamate, ether, thioether or amine function, AA being a hydrophobic amino acid residue, L or D, produced by the coupling between the amine of the amino acid and an acid borne by the group R, said hydrophobic amino acid being selected from the group consisting of tryptophan, tryptophanol, tryptophanamide and 2 indolethylamine, salts thereof of an alkali metal cation, phenylalanine, leucine, isoleucine and valine, and alcohol, amide or decarboxylated derivatives thereof, t represents the mole fraction of the substituent F—R—$[AA]_p$ per glycoside unit, and is between 0.1 and 2, p represents the mole fraction of groups R substituted with AA and is between 0.05 and 1, and wherein when R is not substituted by AA, then the acid(s) of the group R are carboxylates of a cation.

45. A process for preparing the coprecipitate as defined in claim 1, which comprises a coprecipitation step obtained by:
- precipitating the complex between the functionalized dextran and the osteogenic protein by addition of a solution of the calcium salt,
- precipitating the calcium ions by addition of a composition comprising at least one soluble salt of an anion capable of forming an insoluble calcium salt at a given pH, the complex between the functionalized dextran and the osteogenic protein complex being obtained by adding a solution of the functionalized dextran to a solution of the osteogenic protein.

46. The process as claimed in claim 45, in which the precipitation of the calcium salt takes place in the form of calcium phosphate, by addition of a soluble phosphate solution.

* * * * *